US010624644B2

(12) United States Patent
Bakos et al.

(10) Patent No.: US 10,624,644 B2
(45) Date of Patent: Apr. 21, 2020

(54) BATTERY POWERED ELECTROMAGNETIC TISSUE COMPRESSION DEVICE

(71) Applicant: ETHICON LLC, Guaynabo, PR (US)

(72) Inventors: Gregory J. Bakos, Mason, OH (US); Daniel W. Price, Loveland, OH (US); Nicholas B. Van Stolk, Cincinnati, OH (US); John V. Hunt, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 416 days.

(21) Appl. No.: 15/419,102

(22) Filed: Jan. 30, 2017

(65) Prior Publication Data
US 2018/0214151 A1 Aug. 2, 2018

(51) Int. Cl.
*A61B 17/11* (2006.01)
*A61B 17/00* (2006.01)
(Continued)

(52) U.S. Cl.
CPC . *A61B 17/1114* (2013.01); *A61B 2017/00734* (2013.01); *A61B 2017/00876* (2013.01); *A61B 2017/1139* (2013.01); *A61B 2090/309* (2016.02); *A61B 2090/3908* (2016.02); *A61B 2090/3945* (2016.02)

(58) Field of Classification Search
CPC . A61B 17/11; A61B 17/1114; A61B 17/0487; A61B 2017/1117; A61B 2017/1139; A61B 2017/0456; A61B 2017/0458; A61B 17/0057; A61B 17/083; A61B 17/08; A61B 17/12045;
(Continued)

(56) References Cited

U.S. PATENT DOCUMENTS 8,518,062 B2 8/2013 Cole et al.
8,728,105 B2 * 5/2014 Aguirre .............. A61B 17/1114
606/153
(Continued)

FOREIGN PATENT DOCUMENTS

WO WO 2011/100625 A2 8/2011

OTHER PUBLICATIONS

U.S. Appl. No. 15/298,816, filed Oct. 20, 2016.
(Continued)

*Primary Examiner* — Diane D Yabut
(74) *Attorney, Agent, or Firm* — Frost Brown Todd LLC

(57) ABSTRACT

An exemplary tissue compression device for forming an anastomosis between first and second anatomical structures includes a first device portion and a second device portion configured to mate with the first device portion. The first and second device portions are configured to magnetically draw together to compress tissue positioned therebetween. The device further includes a circuit assembly including an electrical element and a battery configured to energize the electrical element. The electrical element may be in the form of an electromagnet or an illumination device, for example. In exemplary versions, the first device portion may include a first circuit assembly having a first electrical element and a first battery, and the second device portion may include a second circuit assembly having a second electrical element and a second battery.

20 Claims, 17 Drawing Sheets

(51) Int. Cl.
*A61B 90/00* (2016.01)
*A61B 90/30* (2016.01)

(58) Field of Classification Search
CPC .. A61B 2017/00575; A61B 2017/0081; F16G 11/105; F16G 11/106
See application file for complete search history.

(56) References Cited

U.S. PATENT DOCUMENTS

| | | | |
|---|---|---|---|
| 9,364,238 B2 | 6/2016 | Bakos et al. | |
| 9,375,137 B2 | 6/2016 | Sherwinter | |
| 2007/0282311 A1* | 12/2007 | Scott | A61B 17/02 606/1 |
| 2009/0048618 A1* | 2/2009 | Harrison | A61B 17/0483 606/153 |
| 2011/0218476 A1* | 9/2011 | Kraemer | A61B 17/1114 604/8 |
| 2011/0295055 A1* | 12/2011 | Albrecht | A61B 5/073 600/37 |

OTHER PUBLICATIONS

U.S. Appl. No. 15/419,086, filed Jan. 30, 2017.
U.S. Appl. No. 15/419,132, filed Jan. 30, 2017.
U.S. Appl. No. 15/419,151, filed Jan. 30, 2017.
U.S. Appl. No. 61/697,845, filed Sep. 7, 2012.
International Search Report and Written Opinion dated Aug. 10, 2018 for Application No. PCT/IB2018/050351, 15 pgs.

* cited by examiner

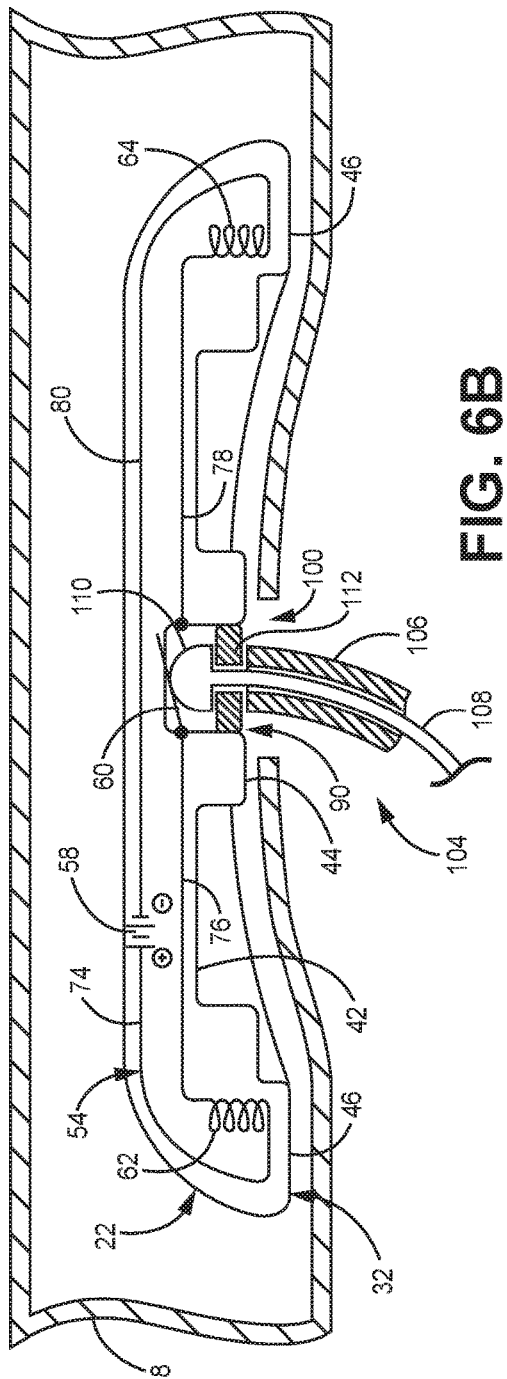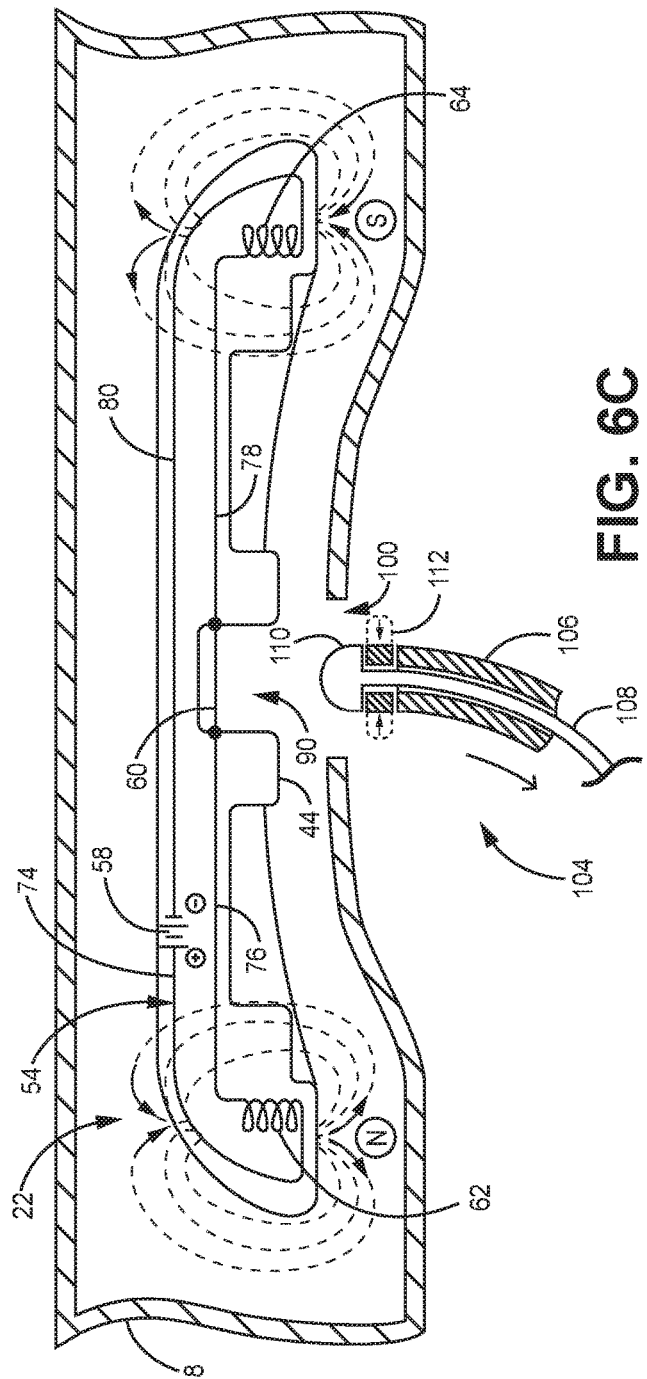

BATTERY POWERED ELECTROMAGNETIC TISSUE COMPRESSION DEVICE

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be positioned adjacent to each other to form an anastomosis between the portions of the duodenum and the ileum in which the enterotomies are formed, as described in greater detail below. The anastomosis establishes direct fluid communication between the adjacent portions of the duodenum and ileum, enabling at least some nutrient-rich chyme to pass through the anastomosis to travel from the duodenum directly to the ileum without passing through the jejunum. In other variations in which the anastomosis is positioned at other locations within the gastrointestinal tract, some chyme may pass through a shortened portion of the jejunum. In either case, the anastomosis enables accelerated passage of nutrient-rich chyme through the gastrointestinal tract.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; and U.S. patent application Ser. No. 15/298,816, entitled "Method for Partial Diversion of the Intestinal Tract," filed Oct. 20, 2016, published as U.S. Pub. No. 2017/0035425 on Feb. 9, 2017, the disclosure of which is incorporated by reference herein.

While a variety of anastomosis devices and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements, and in which:

FIG. 6B depicts a schematic side cross-sectional view of the first device half of FIG. 6A following insertion into the first portion of the small intestine, showing the applier instrument engaged with the first device portion to hold a circuit switch in an open position:

FIG. 6C depicts a schematic side cross-sectional view of the first device half of FIG. 6A following insertion into the first portion of the small intestine, showing the applier instrument disengaged from the first device half and the circuit switch moved to a closed position in which electromagnets of the first device half are energized to generate magnetic fields;

Figure 1:
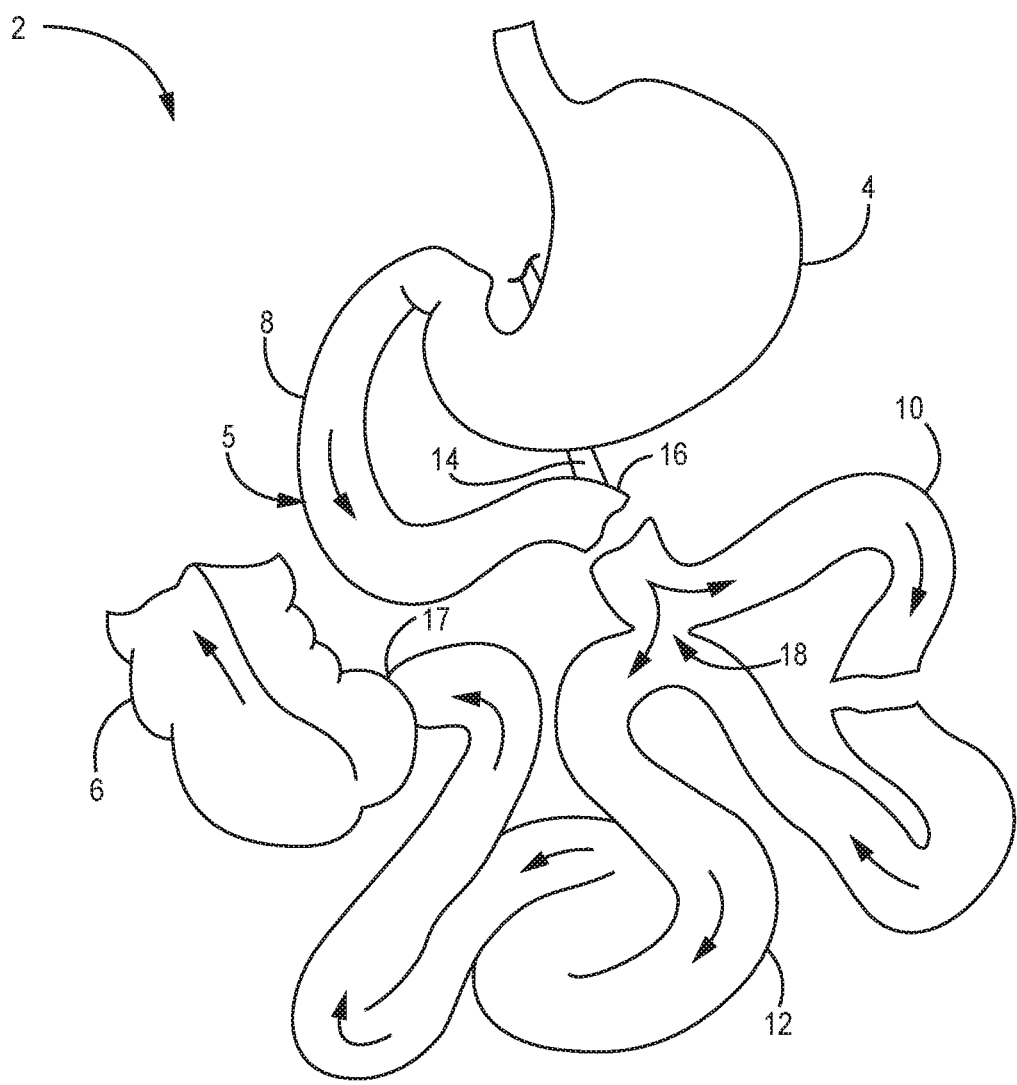
FIG. 1 depicts a diagrammatic view of a portion of a patient's digestive system, showing an exemplary side-by-side anastomosis formed in the small intestine.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Intestinal Anastomosis

As noted above, it may be desirable to provide an anastomosis between two anatomical structures within a patient's body, such as two portions of a patient's gastrointestinal tract. FIG. 1 shows an exemplary portion of a gastrointestinal tract (2) including, in downstream order, a stomach (4), a small intestine (5), and a large intestine (6). The small intestine (5) is subdivided into three portions: the duodenum (8), the jejunum (10), and the ileum (12), listed in downstream order. The duodenum (8) is supported by a suspensory muscle (14) known as the ligament of Treitz, and transitions into the jejunum (10) at the duodenojejunal flexure (16). The ileum (12) transitions into the large intestine (6) at the ileocecal junction (17), also known as the ileocecal valve.

Figure 2:
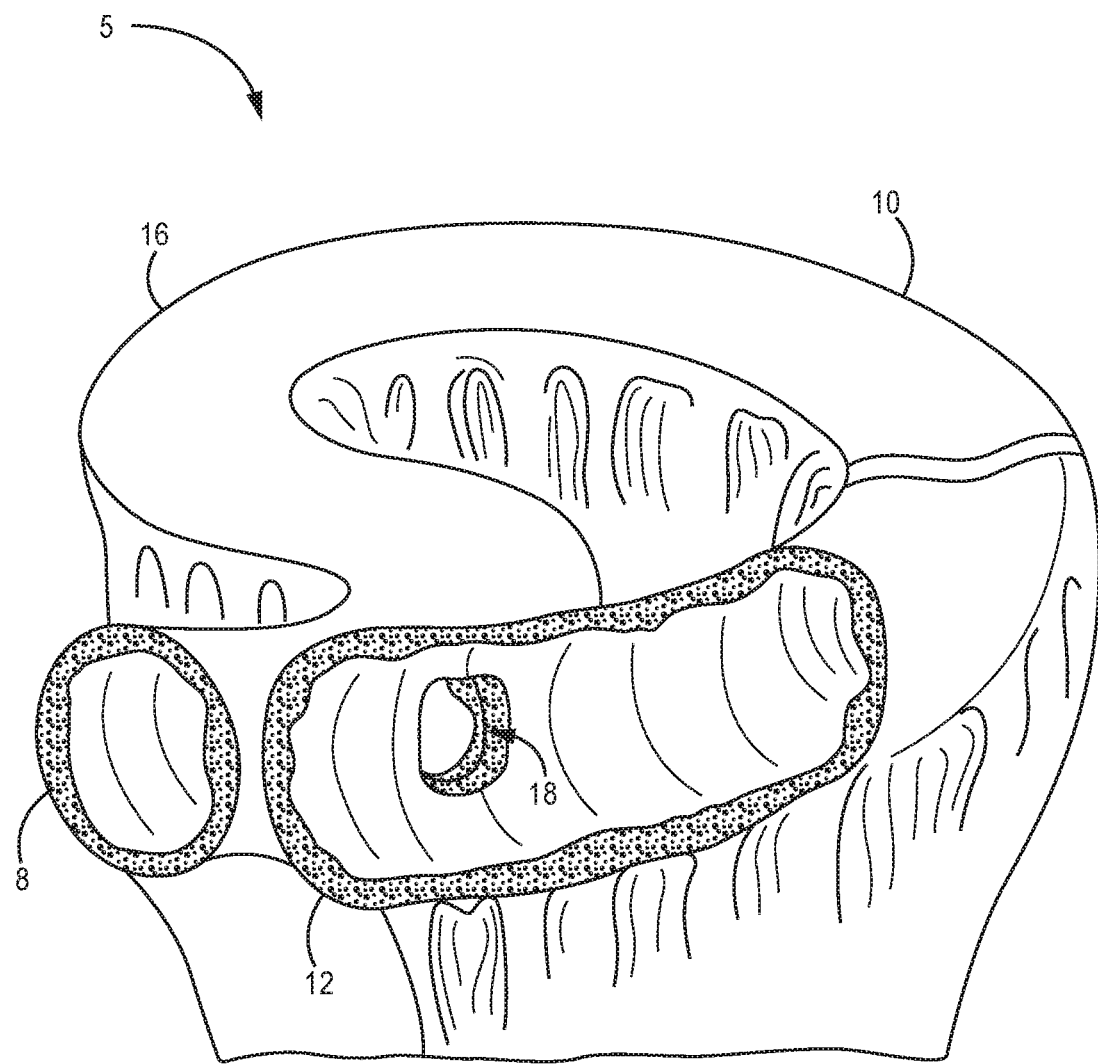
FIG. 2 depicts a partial perspective view of another exemplary side-by-side anastomosis formed in the small intestine.

The gastrointestinal tract (2) is shown including an exemplary anastomosis (18) formed between a proximal portion of the jejunum (10) and the ileum (12). The anastomosis (18) has an inlet side formed through a sidewall of the jejunum (10) at a location adjacent to and downstream of the duodenojejunal flexure (16) and the ligament of Treitz (14). The anastomosis (18) additionally has an outlet side formed through a sidewall of the ileum (12). It will be appreciated that the anastomosis (18) may be positioned at various other suitable locations along the gastrointestinal tract (2). For example, as shown in FIG. 2, the anastomosis (18) may be formed between the duodenum (8) and the ileum (12). Additional exemplary locations of the anastomosis (18) are described in U.S. patent application Ser. No. 15/298,816, entitled "Methods for Partial Diversion of the Intestinal Tract," filed Oct. 20, 2016, published as U.S. Pub. No. 2017/0035425 on Feb. 9, 2017, the disclosure of which is hereby incorporated by referenced herein. It will be further appreciated that the anastomosis (18) may be located elsewhere within a patient's body, other than within the gastrointestinal tract (2). In that regard, it will be understood that the exemplary tissue compression devices shown and described herein may be employed to create anastomoses in various other bodily organs having an internal lumen, and thus are not limited to use in a patient's gastrointestinal tract (2).

Still referring to FIG. 1, the exemplary anastomosis (18) shown provides a pathway for direct fluid communication between the proximal portion of the patient's jejunum (10) and the ileum (12), thereby bypassing a majority of the jejunum (10), located downstream. Consequently, chyme exiting the stomach (4) may flow directly through the duodenum (8), then through the proximal portion of the jejunum (10) and directly into the ileum (12), via the anastomosis (18), without passing through the downstream portion of the jejunum (10). In some instances, a first portion of the chyme exiting the stomach (4) may flow directly from the proximal portion of the jejunum (10) to the ileum (12), via the anastomosis (18). Simultaneously, a second portion of the chyme may pass the anastomosis (18) and flow through the downstream portion of the jejunum (10), rejoining with the first portion of chyme in the ileum (12) before passing into the large intestine (6). Accordingly, the anastomosis (18) may provide a complete diversion or a partial diversion of chyme passing through the jejunum (10).

Forming a side-by-side anastomosis (18) between two portions of the gastrointestinal tract (2), positioned adjacent to one another, may be achieved using a compression device having first and second device portions that clamp intestinal tissue therebetween, as described above. In some procedures, the device portions may be introduced into the intestinal lumen via two or more enterotomies formed in the intestinal sidewalls at respective upstream and downstream locations. In other procedures, the device portions may be introduced into the intestinal lumen endoscopically, using two or more endoscopes inserted through naturally occurring body orifices and directed into the intestinal lumen from opposing directions. The exemplary tissue compression devices disclosed herein may be positioned within a patient using either of these methods, for example.

II. Exemplary Anastomosis Tissue Compression Device Having Electromagnets

As will be described in greater detail below, the first and second portions of the tissue compression devices disclosed herein may include magnetic members that draw the device portions together. The device portions, when drawn together magnetically, compress tissue positioned therebetween with a clamping force sufficient to cause ischemia and eventual necrosis of the tissue. Once necrosis occurs, the device falls away to reveal an anastomosis, and the device is then passed downstream through the gastrointestinal tract (2).

In some instances, it may be desirable to provide selective activation of the magnetic properties of a tissue compression device. For instance, it may be desirable to initially provide tissue compression devices in a non-magnetized state, then transition the tissue compression devices to a magnetized state after the tissue compression devices have been at least initially positioned within the patient. This may facilitate handling of such tissue compression devices in storage and in transit to the anastomosis site in the patient. The following examples include electromagnetic features that enable the operator to initially handle the tissue compression devices in a non-magnetized state, then transition the tissue compression devices to a magnetized state after the tissue compression devices have been at least initially positioned within the patient.

Figure 3:
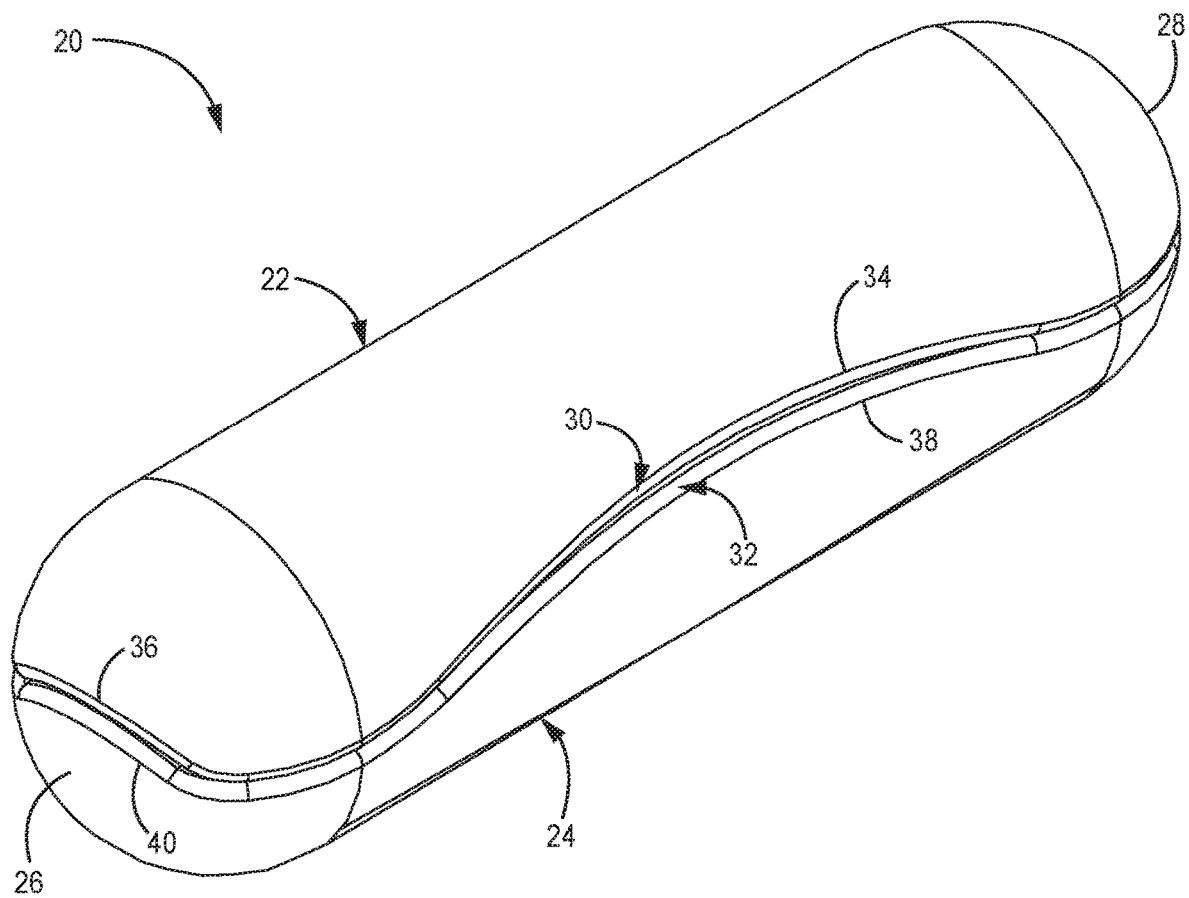
FIG. 3 depicts a perspective view of an exemplary tissue compression device for forming an anastomosis.

A. Structural Features of Exemplary Tissue Compression Device Having Electromagnets FIGS. 3-4B show an exemplary tissue compression device (20) for forming an anastomosis, such as a side-by-side anastomosis, in an assembled configuration. The tissue compression device (20) includes a first device half (22) and a second device half (24) that mate together to define an elongate device body that extends along a longitudinal device axis between a convexly rounded first end (26) and a convexly rounded second end (28). The device (20) of the present example is formed with a length that is greater than its width so as to present a pill-like shape. Each device half (22, 24) may be formed as a unitary structure having non-articulating features, as described below.

Figure 4A:
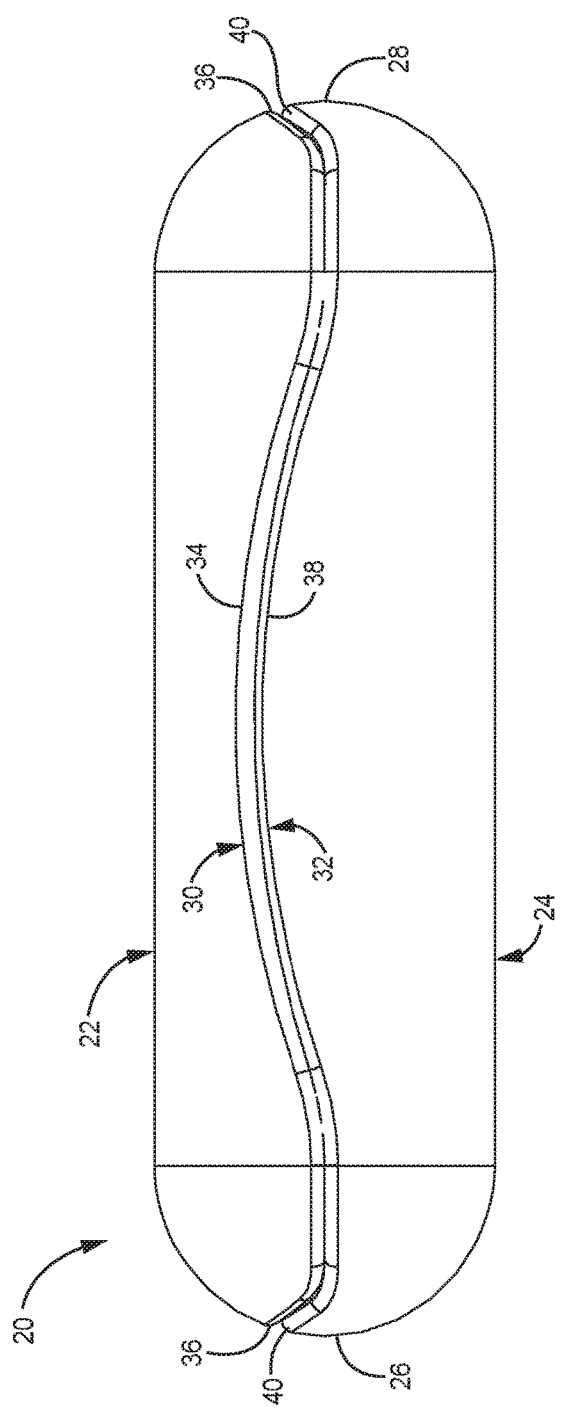
FIG. 4A depicts a side elevational view of the tissue compression device of FIG. 3.
Figure 4B:
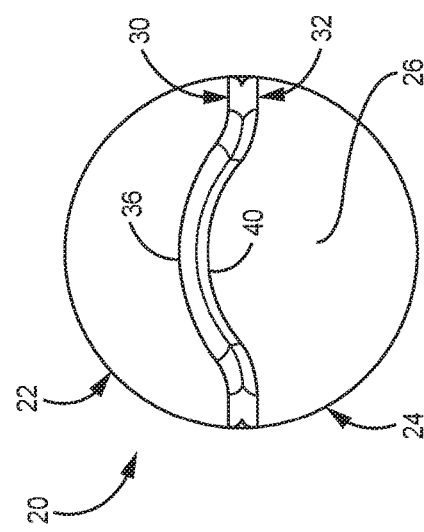
FIG. 4B depicts an end elevational view of the tissue compression device of FIG. 3.

As best shown in FIGS. 4A and 4B, the tissue compression device (20) of the present example is formed with a transverse cross-section having a rounded shape to provide the device (20) with a rounded and smooth outer periphery that is atraumatic to patient tissue. As best shown in FIG. 4B, the exemplary device (20) is formed with a generally circular shaped cross-section. Additionally, as shown in FIG. 4A, the circular cross-section may be uniform in diameter along a medial portion of the device (20) extending between its first and second rounded ends (26, 28). In alternative variations, the device (20) may be formed with a transverse cross-section of various other shapes, such as various rounded shapes, and the cross-section may be uniform or non-uniform (e.g., tapered) along a length of the device (20).

Figure 5:
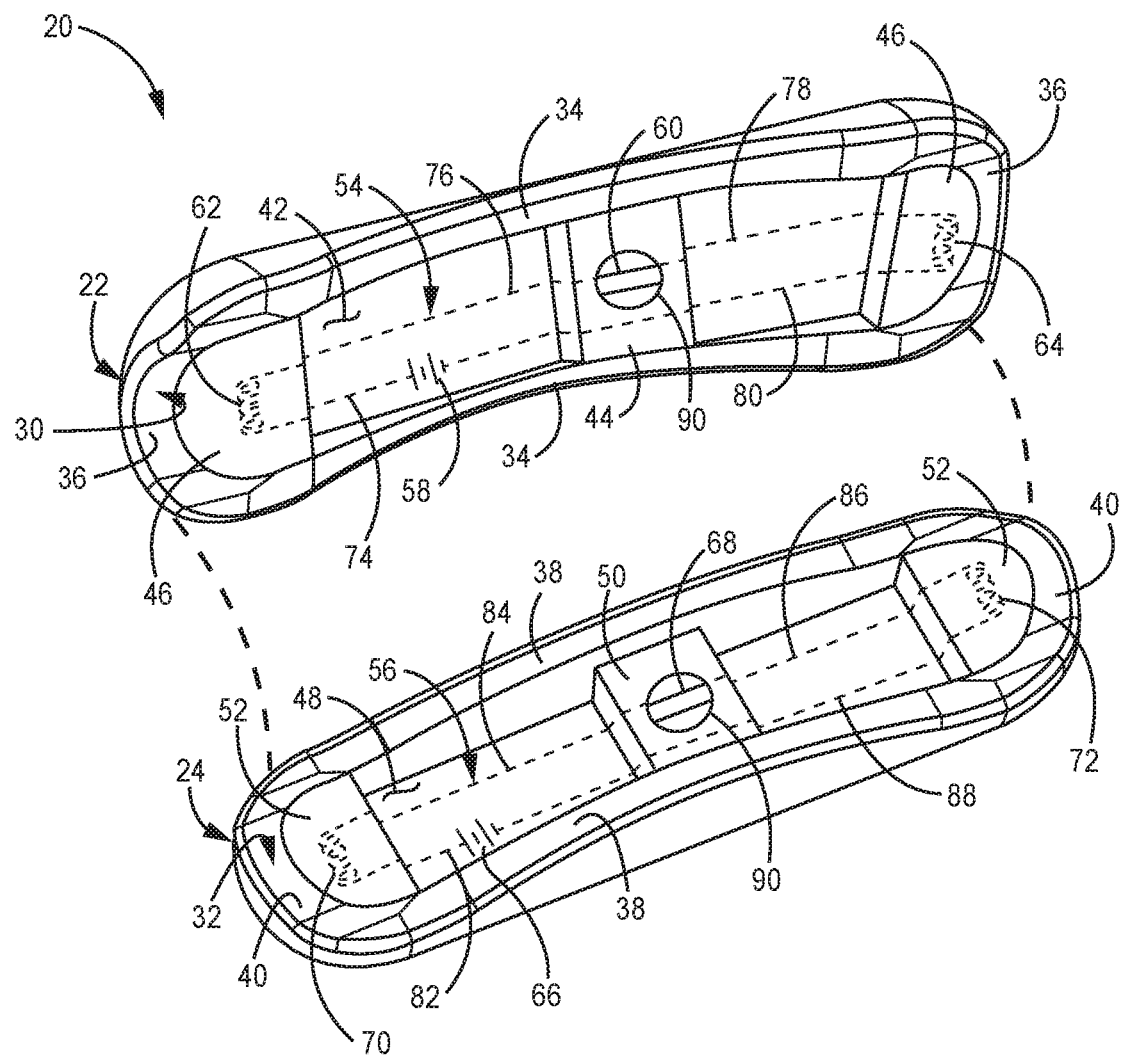
FIG. 5 depicts a disassembled perspective view of the tissue compression device of FIG. 3, showing first and second circuit assemblies thereof schematically.

FIG. 5 shows the device (20) in a disassembled configuration to reveal additional structural features. For illustrative purposes only, the first device half (22) is shown in an upper position and the second device half (24) is shown in a lower position. In that regard, it will be appreciated that relative positional terms including "upper," "lower" and similar terms as may be used herein are illustrative only and are not limiting of the features to which they refer nor of the various orientations in which the device (20) may be employed.

As best shown in FIGS. 4A-5, the first device half (22) includes a first mating surface (30) that extends continuously about a perimeter of the mating side of the first device half (22). Similarly, the second device half (24) includes a second mating surface (32) that extends continuously about a perimeter of the mating side of the second device half (24). In the present example, the first mating surface (30) is formed with a first contour and the second mating surface (32) is formed with a second contour that complements the first contour. More specifically, the first mating surface (30) is formed with elongate concave side portions (34) extending generally parallel to the device axis, and with concave end portions (36) extending generally transverse to the device axis. The second mating surface (32) is formed with elongate convex side portions (38) extending generally parallel to the device axis, and with convex end portions (40) extending generally transverse to the device axis.

As best shown by a comparison of FIGS. 4A and 4B, in the present example, the side portions (34, 38) of the first and second mating surfaces (30, 32) are formed with a first radius of curvature, and the end portions (36, 40) are formed with a second, differing radius of curvature. The mating surfaces (30, 32) may exhibit additional geometric features as disclosed in U.S. patent application Ser. No. 15/419,132, entitled "Elongated Tissue Compression Device System with Smooth Outer Contour and Orthogonal Curved Aligning Surfaces," filed on Jan. 30, 2017, published as U.S. Pub No. 2018/0214149 on Aug. 2, 2018, the disclosure of which is hereby incorporated by reference herein. In other versions, though not shown, the mating surfaces (30, 32) may be formed with various alternative complementary contours, or with fully or partially planar configurations, for example.

Still referring to FIG. 5, the first device half (22) of the present example includes a first recessed base wall (42) from which a central platform (44) and a pair of raised end structures (46) extend in a direction generally toward the device axis. Similarly, the second device half (24) of the present example includes a second recessed base wall (48) from which a central platform (50) and a pair of raised end structures (52) extend in a direction generally toward the device axis. As shown in FIG. 8B, the device halves (22, 24) mate together to define a closed interior cavity bounded at its outer perimeter by the recessed base walls (42, 48) and the raised end structures (46, 52).

As shown schematically in FIG. 5, the first device half (22) includes a first circuit assembly (54) arranged internally within the first device half (22), and the second device half (24) includes a second circuit assembly (56) arranged internally within the second device half (24). The first circuit assembly (54) of the first device half (22) includes a battery (58), a switch (60), and a pair of electrical elements in the form of first and second inductors (62, 64). Similarly, the second circuit assembly (56) of the second device half (24) includes a battery (66), a switch (68), and a pair of electrical elements in the form of third and fourth inductors (70, 72). While the batteries (58, 66) are shown in the form of multi-cell batteries, it will be appreciated that the batteries (58, 66) may alternatively be in the form of single-cell batteries. As described in greater detail below, the inductors (62, 64, 70, 72) are operable as mutually-attracting electromagnets when energized by their respective batteries (58, 66).

The first and second circuit assemblies (54, 56) may be arranged within the bodies of the first and second device halves (22, 24). More specifically, each circuit assembly (54, 56) may be arranged inwardly of the rounded outer periphery of the device (2). In exemplary methods of production, each device half (22, 24) may be injection molded about its respective circuit assembly (54, 56). Alternatively, one or more components of each circuit assembly (54, 56) may be removably mounted within the body of its respective device half (22, 24). For example, though not shown, each device half (22, 24) may include an internal chamber in which one or more components of the respective circuit assembly (54, 56) is received, and to which access may be provided by one or more removable access panels or similar structures.

Referring to FIG. 5 in combination with FIGS. 6B and 6C, the first circuit assembly (54) includes a first circuit leg (74) extending between a positive terminal of the battery (58) and a first contact end of the first inductor (62). A second circuit leg (76) extends between a second contact end of the first inductor (62) and a first contact end of the switch (60). A third circuit leg (78) extends between a second contact end of the switch (60) and a first contact end of the second inductor (64). A fourth circuit leg (80) extends between a second contact end of the second inductor (64) and a negative terminal of the battery (66). Accordingly, the battery (58) electrically couples to the first and second inductors (62, 64) via the circuit legs (74, 76, 78, 80) and the switch (60).

The second circuit assembly (56) may be configured in a manner similar to the first circuit assembly (54). As shown, the second circuit assembly (56) includes a first circuit leg (82) extending between a positive terminal of the battery (66) and a first contact end of the third inductor (70). A second circuit leg (84) extends between a second contact end of the third inductor (70) and a first contact end of the switch (68). A third circuit leg (86) extends between a second contact end of the switch (68) and a first contact end of the fourth inductor (72). A fourth circuit leg (88) extends between a second contact end of the fourth inductor (72) and a negative terminal of the battery (66). Accordingly, the battery (66) electrically couples to the third and fourth inductors (70, 72) via the circuit legs (82, 84, 86, 88) and the switch (68).

In the present example, each of the first and second inductors (62, 64) is arranged within a respective one of the raised end structures (46) of the first device half (22). Similarly, each of the third and fourth inductors (70, 72) is arranged within a respective one of the raised end structures (52) of the second device half (24). Additionally, the switch (60) of the first device half (22) is arranged within the central platform (44), and the switch (68) of the second device half (24) is arranged within the central platform (50). Each of the central platforms (44, 50) includes a respective opening (90) that extends generally transverse to the device axis and provides access to the respective switch (60, 68). The circuit legs (74, 76, 78, 80, 82, 84, 86, 88) of each circuit assembly (54, 56) extend generally longitudinally through the medial body portion of each device half (22, 24), along the recessed base walls (42, 48), between the raised end structures (46, 52). In alternative versions, the components of each circuit assembly (54, 56) may be arranged at various other suitable locations within their respective device half (22, 24) as desired. Additionally, while each circuit assembly (54, 56) is shown having two inductors and one battery, it will be appreciated that various other quantities of these components, in addition to other electrical components, may be provided.

Each switch (60, 68) is shown in the form of a single-pole, single-throw ("SPST") switch, movable between an open position and a closed position. When a switch (60, 68) is in the open position, its respective circuit assembly (54, 56) is deenergized. When a switch (60, 68) is in the closed position, electrical energy from the respective battery (58, 66) flows to and energizes the respective inductors (62, 64, 70, 72). When energized, each inductor (62, 64, 70, 72) functions as an electromagnet and generates a respective magnetic field. As described in greater detail below, each inductor (62, 64, 70, 72) may generate a magnetic field having a polarity opposite that of a magnetic field generated by an opposing inductor (62, 64, 70, 72) of the other device half (22, 24). For example, the first and third inductors (62, 70) may generate magnetic fields of opposite polarity, and the second and fourth inductors (64, 72) may generate magnetic fields of opposite polarity. Consequently, the device halves (22, 24) may magnetically attract one another and draw together to compress tissue positioned therebetween for forming an anastomosis. Further, each switch (60, 68) may be biased toward its closed position by a resilient member (not shown) and held open with an applier instrument (104) to deactivate the magnetic fields until the device half (22, 24) is positioned within an anatomical structure and is ready for use.

The tissue compression device (20) may further include various additional features not shown herein, such as one or more mechanical latching mechanisms, tissue retaining clips, and/or suture bores as disclosed in U.S. patent application Ser. No. 15/419,086, entitled "Magnetic Tissue Compression Device with Backup Mechanical Latch." filed on Jan. 30, 2017, issued as U.S. Pat. No. 10,206,682 on Feb. 19, 2019, the disclosure of which is hereby incorporated by reference herein. Such suture bores may be used in combination with suture materials and methods as disclosed in U.S. patent application Ser. No. 15/419,151, entitled "Tissue Compression Device with Features to Contain Needles and Suture During Packaging and Placement in Body," filed on Jan. 30, 2017, published as U.S. Pub. No. 2018/0214152 on Aug. 2, 2018, the disclosure of which is hereby incorporated by reference herein.

B. Exemplary Procedures for Forming an Anastomosis Using Exemplary Tissue Compression Device Having Electromagnets Referring now to FIGS. 6A-6F, an exemplary procedure will now be described for deploying the device halves (22, 24) of the tissue compression device (20) within the small intestine (5) of a patient at the site of an anastomosis to be formed. The first device half (22) is deployed through a first enterotomy (100) into the duodenum (8), and the second device half (24) is deployed through a second enterotomy (102) into an adjacent portion of the ileum (12). The enterotomies (102, 104) may be formed using any suitable cutting instrument known in the art. While specific reference is made to the duodenum (8) and the ileum (12), it will be understood that the device halves (22, 24) may be deployed at various other locations within the gastrointestinal tract (2), or within other organs, at which an anastomosis is to be formed. Further, while the steps illustrated in FIGS. 6A-6D are shown in connection with deploying the first device half (22), it will be understood that similar steps may be taken to deploy the second device half (24).

Figure 6A:
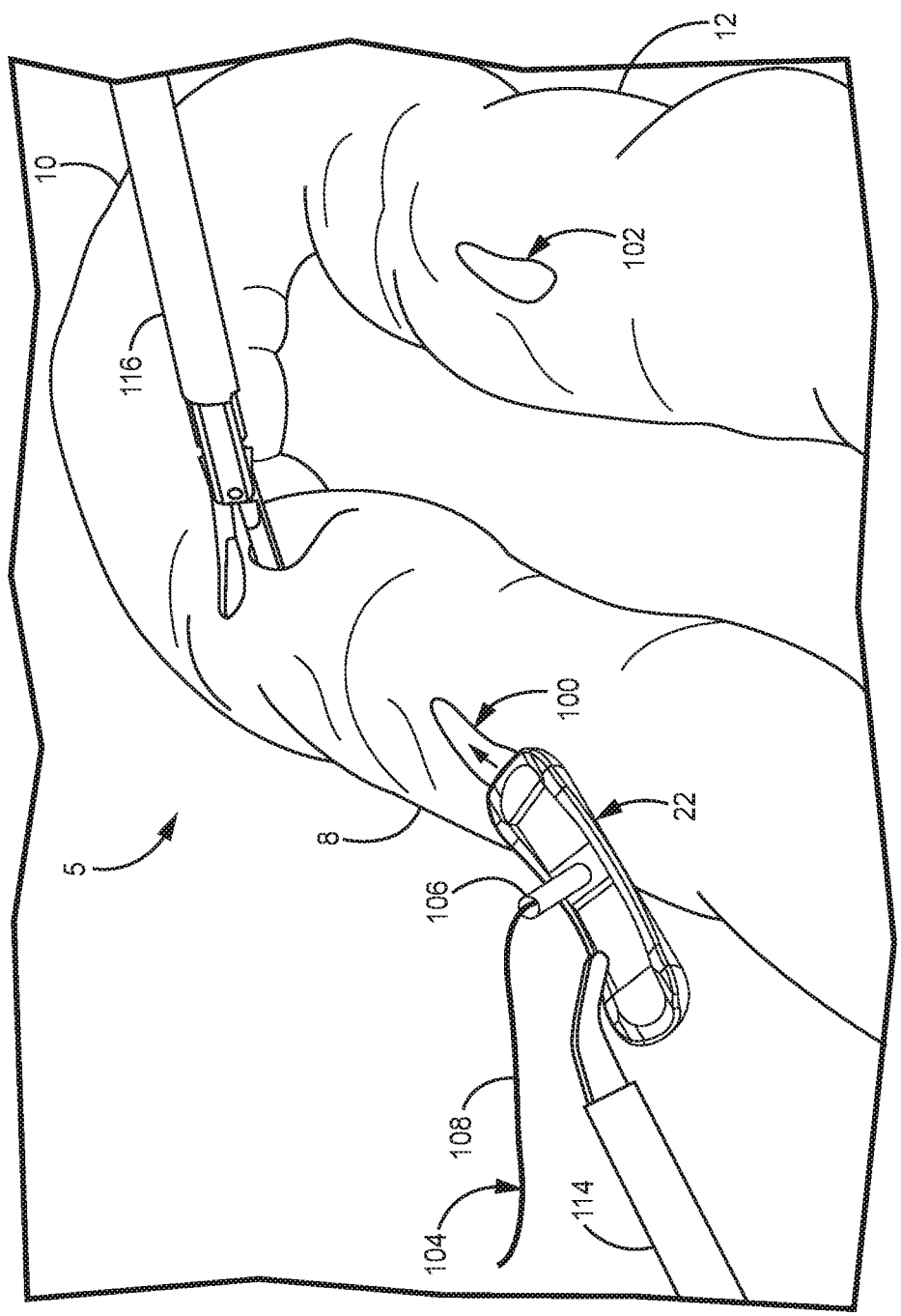
FIG. 6A depicts a perspective view of a patient's small intestine, showing insertion of a first device half of the tissue compression device of FIG. 3, along with an applier instrument, through an enterotomy formed in a portion of the small intestine.

Before deploying each device half (22, 24), an applier instrument (104) is first coupled to the device half (22, 24) to hold the switch (60, 68) in its open position and thereby deactivate the electromagnets (62, 64, 70, 72). As shown in FIGS. 6A-6C, the applier instrument (104) generally includes an outer sheath (106), an elongate shaft member (108) that is slidable through the outer sheath (106), an enlarged bulb tip (110) coupled to a distal end of the elongate shaft member (108), and an elastic collar (112) encircling the distal end of the shaft member (108) and arranged between the bulb tip (110) and a distal end of the outer sheath (106). Each of the components of the applier instrument (104) may be flexible to facilitate positioning of the device half (22, 24) within the patient. The elastic collar (112) may be in the form of a Touhy-Borst ring, and is flexible between a compressed state for coupling the applier instrument (104) with the device half (22, 24), as shown in FIGS. 6A and 6B; and a relaxed state for decoupling the applier instrument (104) from the device half (22, 24), as shown in FIG. 6C.

As shown in FIG. 6B, the bulb tip (110) and elastic collar (112) of the applier instrument (104) are inserted through the opening (90) formed in the central platform (44) of the first device half (22). The bulb tip (110) contacts and urges the switch (60) toward its open position while the elastic collar (112), in its compressed state, frictionally engages the inner wall of the opening (90) to maintain the bulb tip (110) in contact with the switch (60). While the switch (60) is held in its open position, the inductors (62, 64) of the device half (22) remain inactive.

In the present example, applier instrument (104) engages each device half (22, 24) on the same side as the respective mating surface (30, 32) of device half (22, 24). In some other versions, applier instrument (104) engages each device half (22, 24) on the side opposite to the respective mating surface (30, 32) of device half (22, 24).

Returning to FIG. 6A, once the applier instrument (104) has been coupled to the first device half (22), this assembly may be inserted through the first enterotomy (100) formed in the sidewall of the duodenum (8), using a first grasping instrument (114). Simultaneously, the duodenum (8) may be manipulated and stabilized as needed using a second grasping instrument (116). The grasping instruments (114, 116) may be of various suitable types known in the art. FIG. 6B shows the first device half (22) after being positioned within the duodenum (8), through the first enterotomy (100).

As shown in FIG. 6C, once the first device half (22) has been positioned within the duodenum (8), the applier instrument (104) may be released from the device half (22) to activate the electromagnets (62, 64). In particular, the elongate shaft member (108) and its bulb tip (110) may be pushed distally, and/or the outer sheath (106) may be pulled proximally, to allow the elastic collar (112) to return to its relaxed state and disengage the device half (22), allowing the applier instrument (104) to be pulled away proximally. Upon removal of the bulb tip (110) from the opening (90), the switch (60) springs to its closed position, thereby completing the circuit and allowing electrical energy to flow from the battery (58) to the first and second inductors (62, 64) via the switch (60) and the circuit legs (74, 76, 78, 80). The same process may then be repeated for deploying the second device half (24) within the ileum (12) through the second enterotomy (102).

As indicated by symbols "N" and "S" shown in FIG. 6C, the inductors (62, 64) of the first device half (22) generate magnetic fields of opposite polarities in the present example. The inductors (70, 72) of the second device half (24) are configured to operate in a similar manner, to facilitate proper alignment of the first and second device halves (22, 24) during use. For example, the first and third inductors (62, 70) may generate magnetic fields of opposite polarities to magnetically attract one another when energized, and the second and fourth inductors (64, 72) may generate magnetic fields of opposite polarities to magnetically attract one another when energized.

Figure 6D:
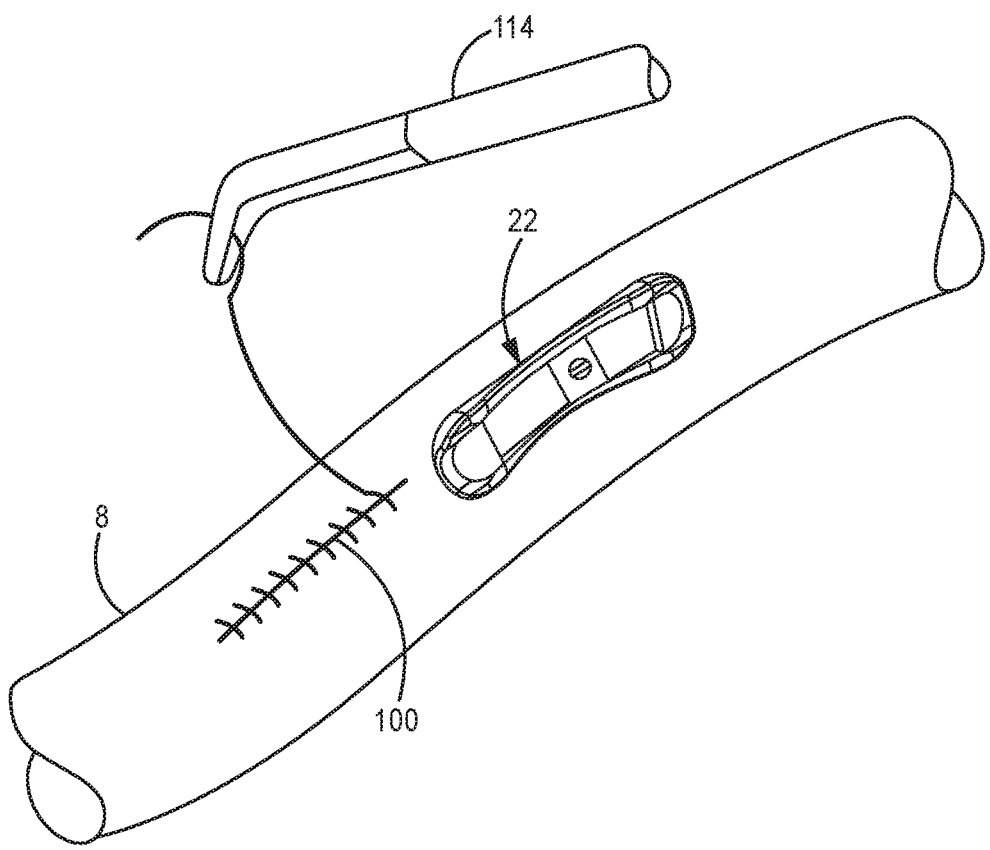
FIG. 6D depicts a perspective view of the first portion of the small intestine containing the first device half of FIG. 6A, showing suturing of the enterotomy following removal of the applier instrument.
Figure 6E:
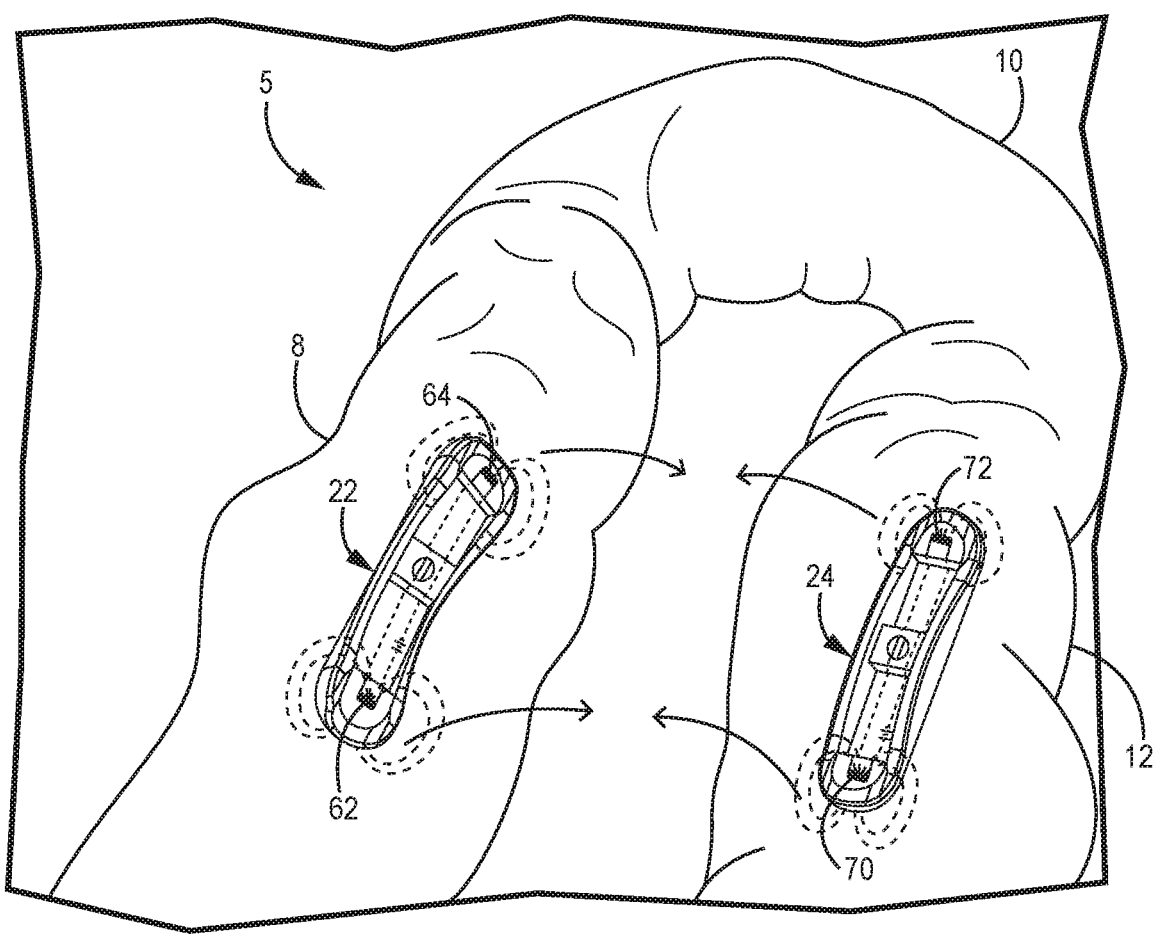
FIG. 6E depicts a perspective view of the small intestine after deployment of the first and second device halves of the tissue compression device of FIG. 3 into respective adjacent portions of the small intestine using the exemplary procedure of FIGS. 6A-6D.

As shown in FIG. 6D, after each device half (22, 24) is deployed within its respective portion of the small intestine (5), the enterotomies (100, 102) are sutured closed with an instrument (114). Alternatively, the enterotomies (100, 102) may remain open in versions in which the device halves (22, 24) are provided with tissue retaining clips, as disclosed in U.S. patent application Ser. No. 15/419,086, issued as U.S. Pat. No 10,206,682 on Feb. 19, 2019, incorporated by reference above. FIG. 6E shows the first device half (22) positioned within the duodenum (8) and the second device half (24) positioned within an adjacent portion of the ileum (12). As indicated by directional arrows, the adjacent portions of the duodenum (8) and the ileum (12) may then be repositioned to arrange the device halves (22, 24) in confronting relation.

Figure 6F:
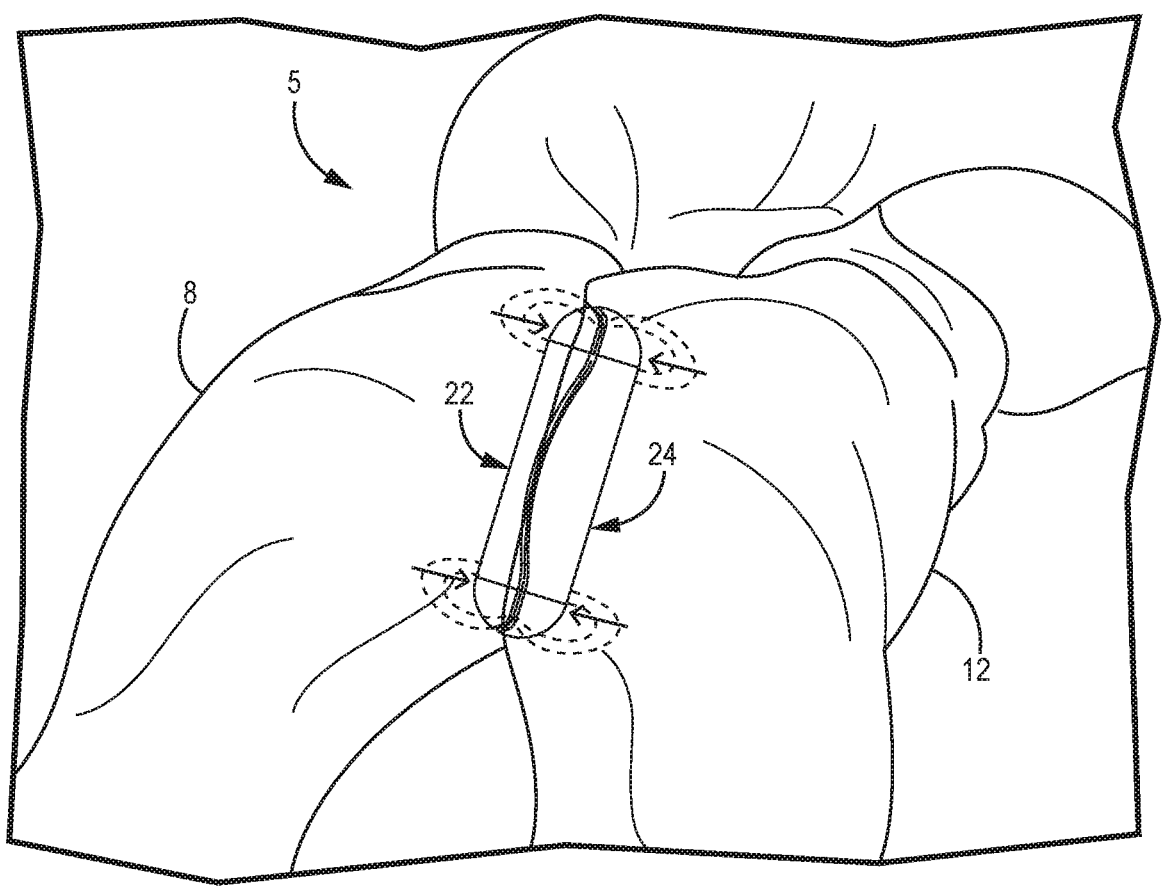
FIG. 6F depicts a perspective view of the small intestine after deployment of the first and second device halves of the tissue compression device of FIG. 3, showing the first and second device halves magnetically drawing together to compress intestinal tissue therebetween for forming an anastomosis.

As shown in FIG. 6F, once the device halves (22, 24) are brought within proximal range of each another, the magnetic fields generated by the inductors (62, 64, 70, 72) mutually attract one another and draw the two device halves (22, 24) together. As described in greater detail below in connection with FIGS. 8A-8C, the device halves (22, 24) thereby compress the sidewalls of the duodenum (8) and the ileum (12) between their mating surfaces (30, 32), and cause the formation of an anastomosis.

In the procedure described above, enterotomies (100, 102) are closed (as shown in FIG. 6D) before device halves (22, 24) and the duodenum (8) and the ileum (12) are finally positioned (as shown in FIGS. 6E and 6F). In some other procedures, enterotomies (100, 102) may remain open until after device halves (22, 24) and the duodenum (8) and the ileum (12) are finally positioned. For instance, this may be desirable when the final positioning of device halves (22, 24), the duodenum (8), and the ileum (12) is accomplished using instruments that are inserted through enterotomies (100, 102). In such procedures, after device halves (22, 24) and the duodenum (8) and the ileum (12) are finally positioned, and after the positioning instruments are withdrawn from the enterotomies (100, 102), the enterotomies (100, 102) may be closed as shown in FIG. 6D.

Figure 7A:
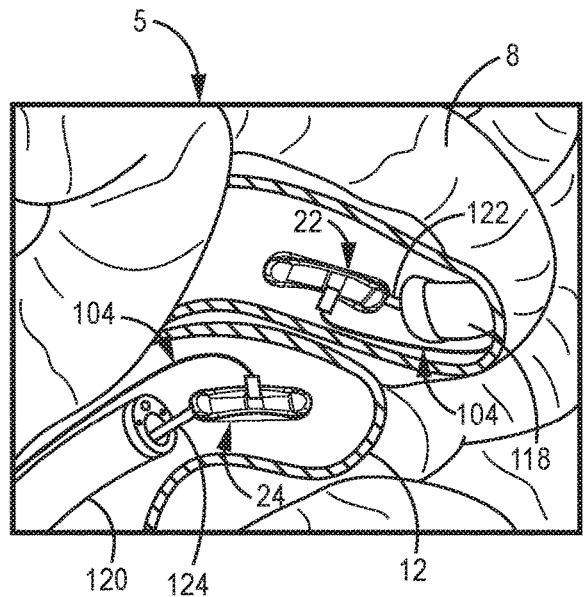
FIG. 7A depicts a partial perspective view of the patient's small intestine, showing another exemplary procedure for deploying the tissue compression device of FIG. 3 within the small intestine using endoscopes.
Figure 7B:
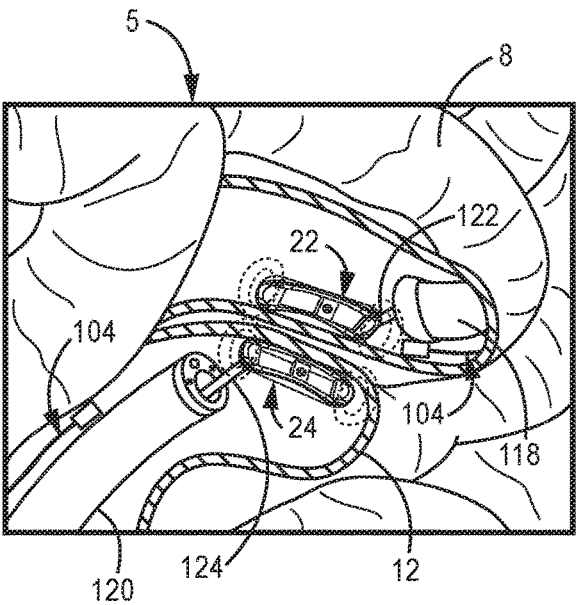
FIG. 7B depicts a partial perspective view of the procedure of FIG. 7A, showing the first and second device halves being aligned with one another within their respective adjacent portions of the small intestine, using the endoscopes.
Figure 7C:
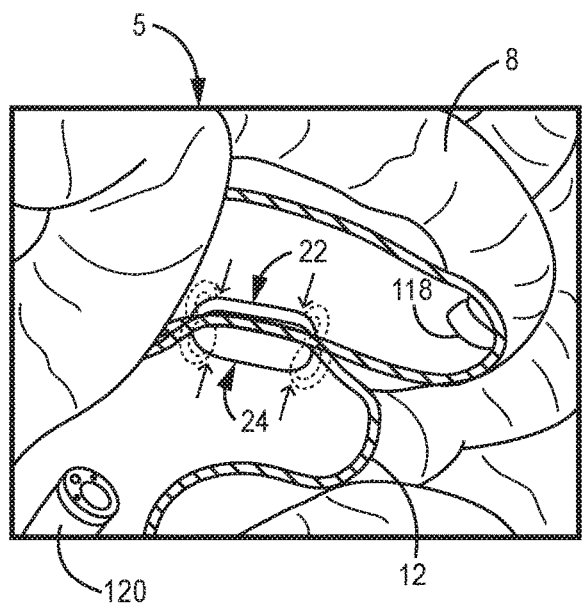
FIG. 7C depicts a partial perspective view of the procedure of FIG. 7A, showing the first and second device halves disengaged from the endoscopes and magnetically drawing together to compress tissue therebetween for forming an anastomosis.

As described above, the exemplary device deployment procedure shown in FIGS. 6A-6F includes the formation of enterotomies (100, 102) in the patient's gastrointestinal tract (2). In some instances, it may be desirable to avoid formation of enterotomies. FIGS. 7A-7C show an exemplary alternative device deployment procedure in which the device halves (22, 24) are deployed within the patient's gastrointestinal tract (2) using endoscopes (118, 120), and without forming enterotomies. While specific reference is made below to the duodenum (8) and the ileum (12), it will be understood that this exemplary procedure may be used for deploying the device halves (22, 24) at various other locations within the gastrointestinal tract (2), or within other organs, at which an anastomosis is to be formed.

Referring to FIG. 7A, the first device half (22) is loaded onto a retractable inner member (122) of the first endoscope (118) and the second device half (24) is loaded onto a retractable inner member (124) of the second endoscope (120). As shown, an applier instrument (104) has already been coupled to each of the device halves (22, 24), in the manner described above. The endoscopes (118, 120) may be of any suitable types known in the art. The first endoscope (118) and respective applier instrument (104) are then inserted through a first natural body orifice (e.g., mouth) at a first end of the patient's gastrointestinal tract (2), and the second endoscope (120) and respective applier instrument (104) are inserted through a second natural body orifice (e.g., rectum) located at a second end of the gastrointestinal tract (2). The distal ends of the endoscopes (118, 120), loaded with the device halves (22, 24) coupled with their respective applier instruments (104), are then routed through the gastrointestinal tract (2), from opposing directions, toward a site at which an anastomosis is to be formed.

Referring to FIG. 7B, the exemplary site for anastomosis formation is shown selected at adjacent portions of the patient's duodenum (8) and ileum (12). Upon reaching the anastomosis site, the endoscopes (118, 120) are manipulated to approximately align the device halves (22, 24) so that their mating surfaces (30, 32) (see FIG. 5) confront one another. The applier instruments (104) are then released from the device halves (22, 24) to activate the electromagnets (62, 64, 70, 72), as described above, and the device halves (22, 24) magnetically attract one another through the tissue sidewalls (8, 12). As shown in FIG. 7C, the device halves (22, 24) draw together magnetically and compress the tissue sidewalls (8, 12) therebetween, thereby holding the device halves (22, 24) securely in place relative to each other and relative to the tissue sidewalls (8, 12). The inner members (122, 124) of the endoscopes (118, 120) are then detached from the device halves (22, 24) and retracted, and the endoscopes (118, 120) and applier instruments (104) are removed from the patient by reversing them through the gastrointestinal tract (2).

Figure 8A:
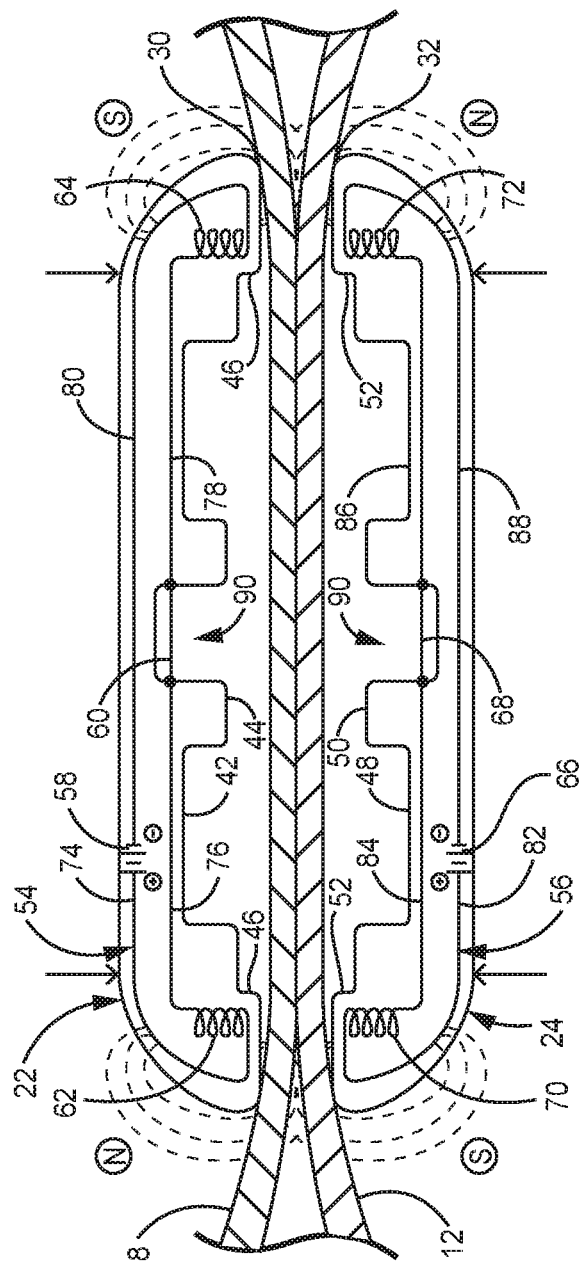
FIG. 8A depicts a schematic side cross-sectional view of the tissue compression device of FIG. 3 following deployment within first and second portions of a patient's small intestine, showing the first and second device halves magnetically drawing together to compress tissue therebetween.
Figure 8B:
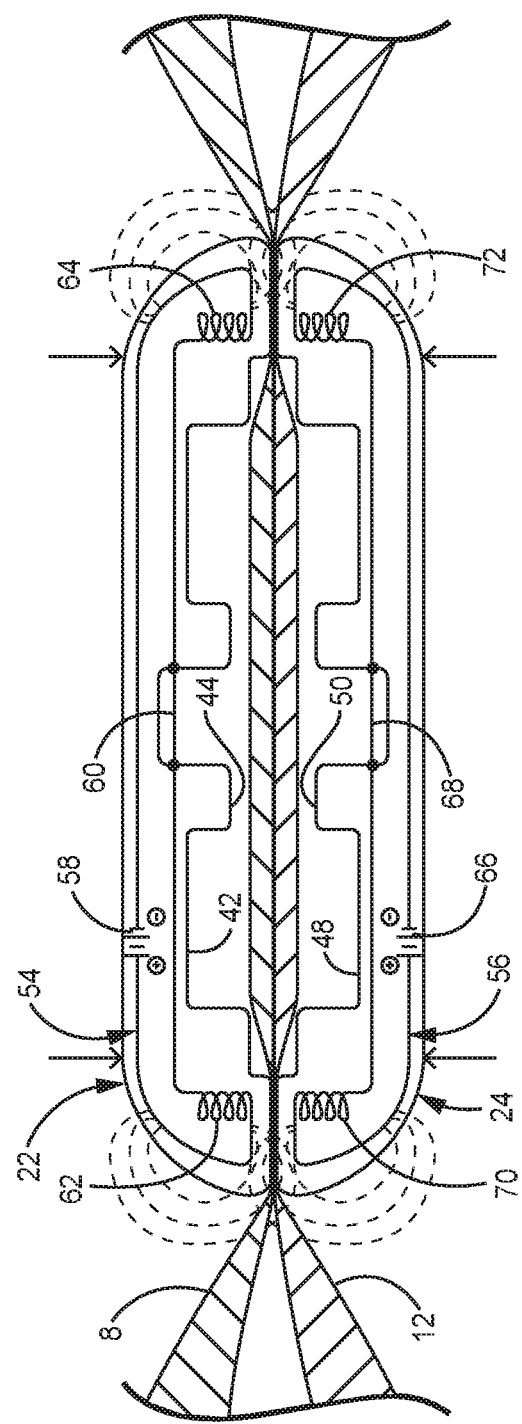
FIG. 8B depicts a schematic side cross-sectional view of the tissue compression device of FIG. 3 in the first and second portions of the patient's small intestine of FIG. 8A, showing further compression of the tissue between the device halves and resulting necrosis of the compressed tissue.
Figure 8C:
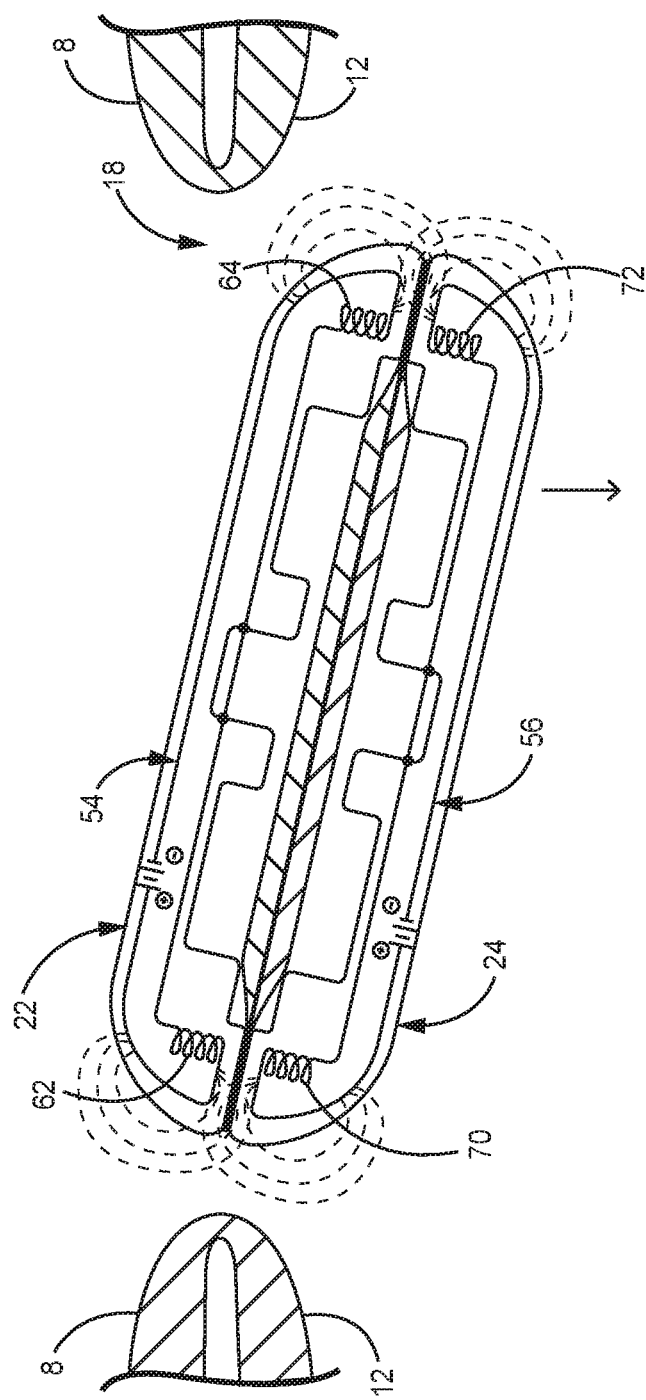
FIG. 8C depicts a schematic side cross-sectional view of the tissue compression device of FIG. 3 in the first and second portions of the patient's small intestine of FIGS. 8A and 8B, showing the compressed tissue in a fully necrosed state, and the device falling away to reveal an anastomosis between the two portions of the small intestine.

FIGS. 8A-8C show formation of an exemplary anastomosis (18) in sidewalls of the patient's duodenum (8) and ileum (12). The device halves (22, 24) are deployed within these portions of the small intestine (5) using either of the two procedures described above in connection with FIGS. 6A-7C, for example. In that regard, it will be understood that the device engagement steps described below, and the resulting anastomosis formation, may apply regardless of the technique used to initially position the device halves (22, 24) within the patient.

Starting with FIG. 8A, the first device half (22) is shown engaging an inner surface of the duodenum (8), and the second device half (24) is shown engaging an inner surface of an adjacent portion of the ileum (12). The duodenum (8) and ileum (12) have been positioned so that the device halves (22, 24) confront one another. Such positioning brings the first and second electromagnets (62, 64) into close enough range with the third and fourth electromagnets (70, 72) that the electromagnets (62, 64.70, 72) magnetically attract one another and draw the two device halves (22, 24) together.

As shown in FIG. 8B, the magnetic attraction provided by the electromagnets (62, 64, 70, 72) operates to compress the sidewalls of the duodenum (8) and the ileum (12) between the mating surfaces (30, 32) of the device halves (22, 24). This compression induces serosa-to-serosa adhesion between the sidewalls (8, 12), about the outer perimeter of the tissue compression device (20). Additionally, the compressive clamping force exerted by the mating surfaces (30, 32) is sufficient to cause ischemia and eventual necrosis in the clamped tissue (8, 12). With passage of time, such as approximately four days to two weeks, for example, the compressed tissue fully necroses and detaches from the surrounding healthy tissue of the sidewalls (8, 12).

As shown in FIG. 8C, detachment of the necrosed tissue from the surrounding healthy tissue (8, 12) releases the tissue compression device (20) into the small intestine (5), and reveals a formed anastomosis (18). The device (20) continues on through the large intestine (6) and is eventually passed by the patient. Advantageously, the smooth outer periphery and low-profile configuration of the device (20) facilitates downstream passage of the device (20) through the gastrointestinal tract (2), including the ileocecal valve (17), for example.

III. Exemplary Anastomosis Tissue Compression Device Having Illumination Device

As noted above, tissue compression device halves (22, 24) are positioned in a confronting arrangement during installation of tissue compression device (20), such that it is necessary for the operator to position halves (22, 24) across from each other with tissue of sidewalls (8, 12) between halves (22, 24). In some instances, it may be difficult for the operator to determine how well the device halves (22, 24) are aligned with one another when positioning the halves (22, 24) within the patient. Substantial misalignment of the device halves (22, 24) can result in the halves (22, 24) sliding across and binding tissue between their mating surfaces (30, 32) when drawing together under magnetic force. Undesirably, such binding of tissue can hinder the anastomosis formation process. While magnetic attraction provided by magnetic members, such as electromagnets (62, 64, 70, 72), may assist in achieving a final stage of alignment of the device halves (22, 24), it may be desirable to provide additional features that assist the operator in making gross positional adjustments during initial stages of alignment, so that final alignment provided by the magnetic members consists of only fine positional corrections, if any. The following example provides a variation of tissue compression device (20) where light is used to assist in guiding the operator to position halves (22, 24) into initial alignment with one another so that magnetic members may complete the confronting alignment of halves (22, 24) with minimal or no binding of tissue between their mating surfaces (30, 32).

Figure 9:
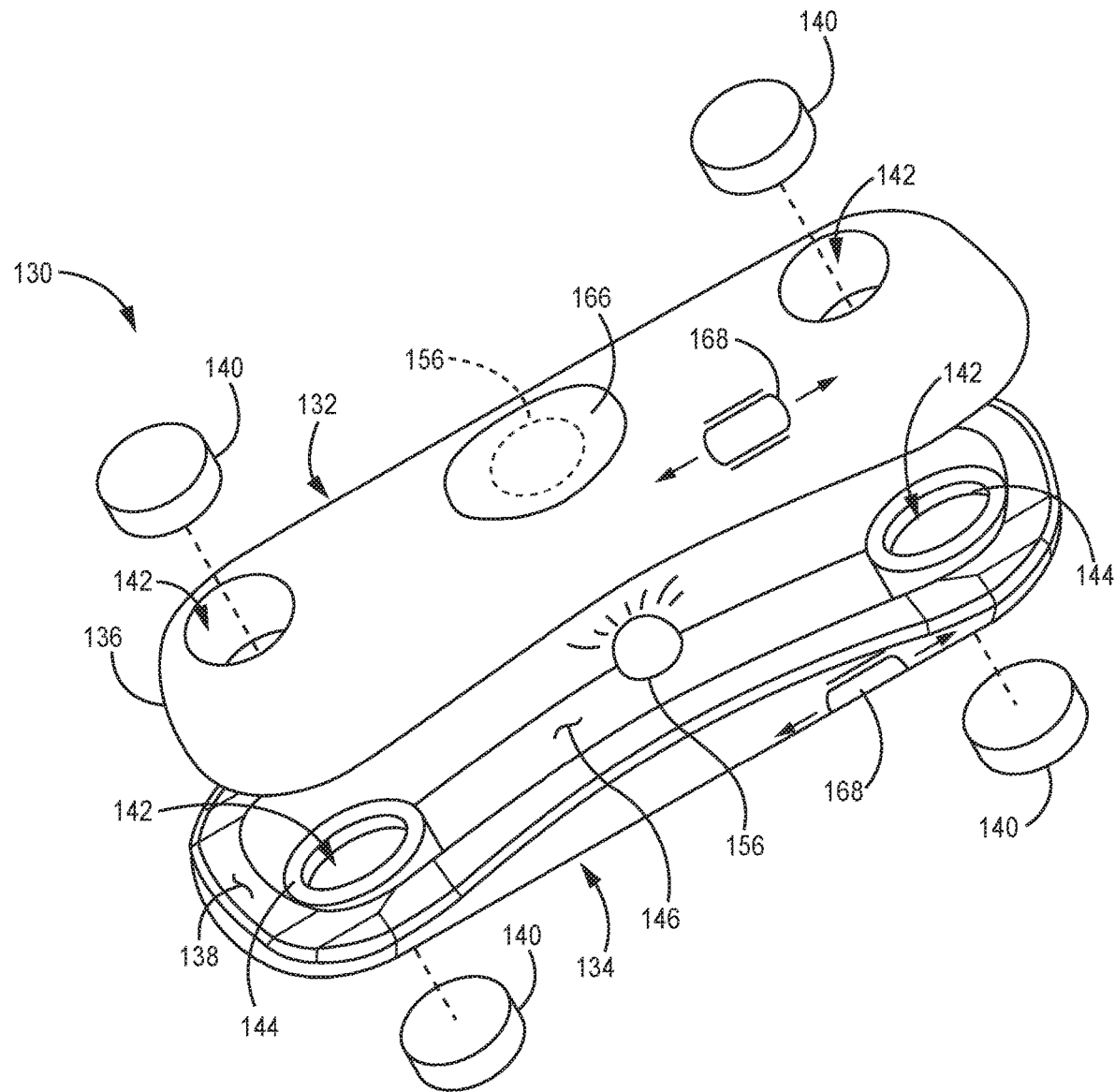
FIG. 9 depicts a disassembled perspective view of another exemplary tissue compression device for forming an anastomosis.

A. Structural Features of Exemplary Tissue Compression Device Having Illumination Devices FIG. 9 shows an exemplary alternative tissue compression device (130) for forming an anastomosis, such as a side-by-side anastomosis, in a disassembled configuration. The tissue compression device (130) includes a first device half (132) and a second device half (134) that mate together to define an elongate device body that extends along a longitudinal device axis between convexly rounded first and second ends similar to ends (26, 28) of tissue compression device (20).

Similar to tissue compression device (20) described above, tissue compression device (130) of the present example is formed with a length that is greater than its width so as to present a pill-like shape. Additionally, device (130) of the present example is formed with a transverse cross-section having a rounded shape to provide the device (130) with a rounded and smooth outer periphery that is atraumatic to patient tissue. Further, the device (130) includes first and second mating surfaces (136, 138) that may be similar in geometric arrangement and function to the first and second mating surfaces (30, 32), respectively, of device (20). Accordingly, the outer periphery of device (130) may be similar in geometric configuration to that of device (20) described above. Unique features of device (130) are described in greater detail below.

Figure 10A:
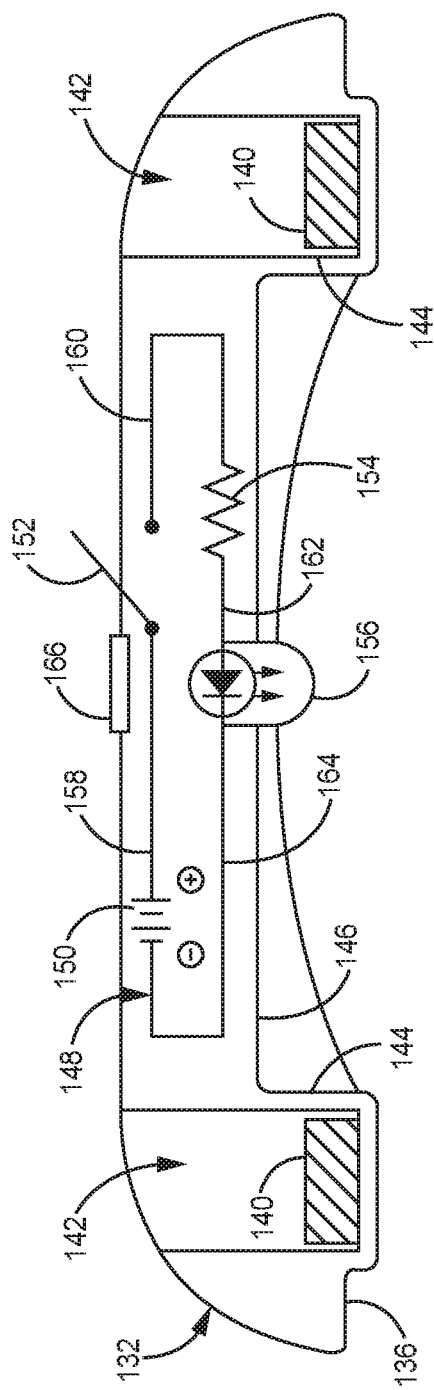
FIG. 10A depicts a schematic side cross-sectional view of a first device half of the tissue compression device of FIG. 9, showing a circuit switch in an open position and an illumination device in a deenergized state.
Figure 10B:
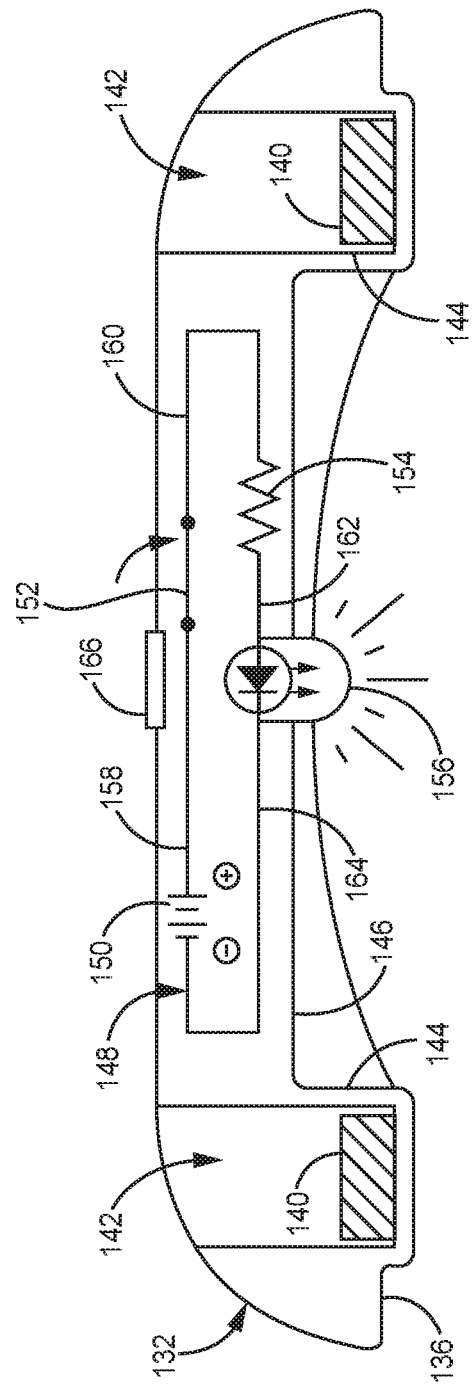
FIG. 10B depicts a schematic side cross-sectional view of the first device half of FIG. 10A, showing the circuit switch in a closed position and the illumination device in an energized state in which it produces light.

Referring to FIGS. 9-10B, the first device half (132) of tissue compression device (130) houses a first pair of magnetic members (140), and the second device half (134) houses a second pair of magnetic members (140). Whereas the magnetic members of device (20) are shown in the form of electromagnets (62, 64, 70, 72), the magnetic members (140) of device (130) are shown in the form of permanent magnets. In alternative versions, however, the magnetic members (140) may be in the form of electromagnets similar to electromagnets (62, 64, 70, 72) described above, or the magnetic members (140) may be provided in addition to electromagnets.

Each magnetic member (140) is received within a respective socket (142) of a respective magnet retaining structure (144) arranged at a respective end of the corresponding device half (132, 134). Each socket (142) extends generally transversely to the device axis, and opens at a first end to the rounded outer periphery of the respective device half (132, 134), and opens at a second end to the mating side of the device half (132, 134). The magnet retaining structures (144) project from a recessed base wall (146) of the respective device half (132, 134), and extend generally transversely toward the device axis.

In the present example, each magnetic member (140) is generally disc-like or cylindrical in shape, and is fixed at an inner end of its respective socket (142), such as by bond or press fit, for example. Alternatively, the magnetic members (140) may be threadedly engaged with their sockets (142), or one or more of the magnetic members (140) may be slidable within its socket (142) and provided with a latching feature configured to lockingly engage an opposing magnetic member (140) of the other device half (132, 134), as disclosed in U.S. patent application Ser. No. 15/419,086, issued as U.S. Pat. No. 10,206,682 on Feb. 19, 2019, incorporated by reference above.

As shown schematically in FIGS. 10A and 10B, each device half (132, 134) of the present example includes a circuit assembly (148) arranged internally within the device half (132, 134). While only the first device half (132) and its circuit assembly (148) is shown, it will be understood that the second device half (134) may include a circuit assembly (148) that is identical in configuration. The circuit assembly (148) of the present example generally includes a battery (150), a switch (152), a resistor (154), and an illumination device (156), shown in the form of a light emitting diode ("LED"). In alternative versions, the illumination device (156) may be in the form of various other suitable light sources. In some versions, the illumination device (156) may be configured to operate in multiple illumination modes, in which the device (156) emits different corresponding types of light having visibly unique characteristics relating to color, intensity, and/or frequency of emission (e.g., blinking), for example, as discussed in greater detail below. Further, while the circuit assembly (148) is shown including only one illumination device (156), it will be understood that various other quantities of illumination devices (156) may be provided.

A first circuit leg (158) of the circuit assembly (148) extends between a positive terminal of the battery (150) and a first contact end of the switch (152). A second circuit leg (160) extends between a second contact end of the switch (152) and a first contact end of the resistor (154). A third circuit leg (162) extends between a second contact end of the resistor (154) and a first contact end of the illumination device (156). A fourth circuit leg (164) extends between a second contact end of the illumination device (156) and a negative terminal of the battery (150). Accordingly, the battery (150) electrically couples to the illumination device (156) via the circuit legs (158, 160, 162, 164) and the switch (152).

As shown in FIGS. 10A and 10B, the circuit legs (158, 160, 162, 164), the battery (150), the switch (152), the resistor (154), and the electrical contact ends of the illumination device (156) may be contained within an interior of the body of the device half (132, 134). A light-emitting end of the illumination device (156) projects from the interior through the recessed base wall (146) and is directed toward the device axis. The illumination device (156) may be arranged centrally between the magnet retaining structures (144), along the device axis. Additionally, each device half (132, 134) of the present example includes a sight window (166) that allows a user to view through the rounded outer periphery of the device half (132, 134) and confirm whether the illumination device (156) is illuminated. The sight window (166) may be transparent or translucent, for example.

The switch (152) is shown in the form of a single-pole, single-throw ("SPST") switch, movable between an open position, shown in FIG. 10A, and a closed position, shown in FIG. 10B. As shown in FIG. 9, an actuator element (168) is mounted to the rounded outer periphery of each device half (132, 134) and couples to the respective switch (152) for selectively moving the switch (152) between its open and closed positions. For example, each actuator element (168) may be moved toward a first end of the device half (132, 134) for placing the switch (152) in its open position, and toward a second end of the device half (132, 134) for placing the switch (152) in its closed position. When the switch (152) is in the open position, as shown in FIG. 10A, the circuit assembly (148) is deenergized. When the switch (152) is moved to its closed position, as shown in FIG. 10B, electrical energy from the battery (150) flows to and energizes the illumination device (156), causing the illumination device (156) to emit light in a direction toward the device axis.

While actuator element (168) is used in the present example to selectively open and close switch (152), it should be understood that various other suitable kinds of devices and techniques may be used to selectively open and close switch (152). By way of example only, tissue compression device (130) may be configured to interact with an instrument like applier instrument (104) described above. In such versions, applier instrument (104) may be configured to hold switch (152) in an open state while applier instrument (104) is coupled with tissue compression device (130); then transition switch (152) to a closed state when applier instrument (104) is decoupled from tissue compression device (130). Similarly, tissue compression device (20) may be modified to include a feature like actuator element (168), such that an operator must actuate actuator element (168) in order to energize electromagnets (62, 64, 70, 72). In such versions, actuator element (168) may effectively replace the operability of applier instrument (104) to selectively transition switch (60, 68) from an open configuration to a closed configuration, such that applier instrument (104) may be omitted in such variations.

Figure 11A:
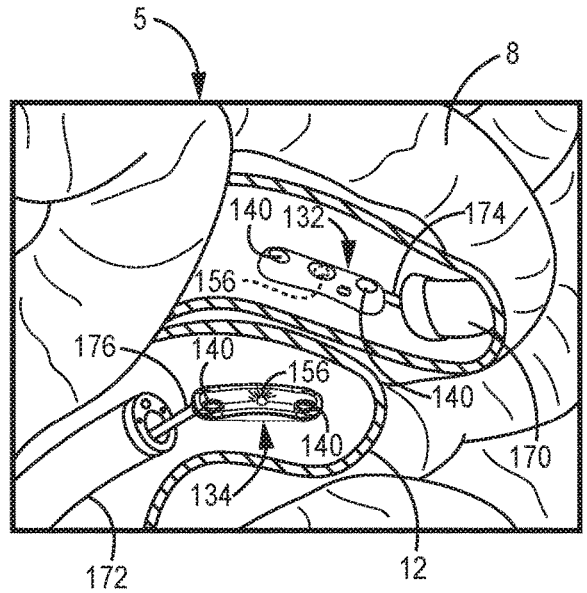
FIG. 11A depicts a partial perspective view of a patient's small intestine, showing an exemplary procedure for deploying the tissue compression device of FIG. 9 within the small intestine using endoscopes.
Figure 11B:
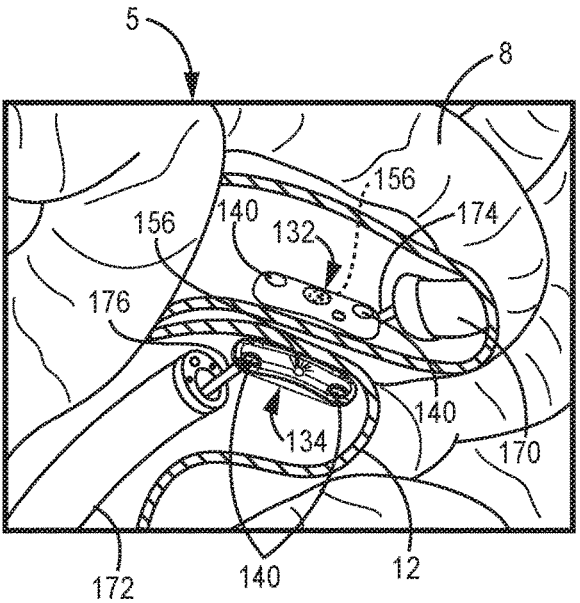
FIG. 11B depicts a partial perspective view of the procedure of FIG. 11A, showing the first and second device halves being aligned with one another within their respective adjacent portions of the small intestine, using the endoscopes.
Figure 11C:
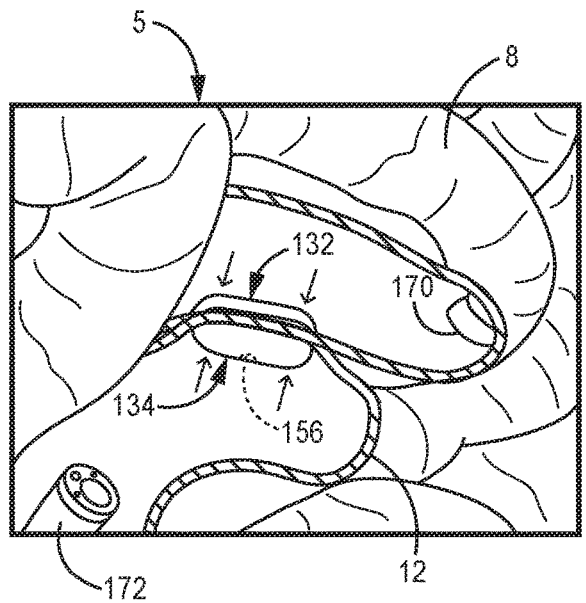
FIG. 11C depicts a partial perspective view of the procedure of FIG. 11A, showing the first and second device halves disengaged from the endoscopes and magnetically drawing together to compress tissue therebetween for forming an anastomosis.

B. Exemplary Procedure for Deploying Tissue Compression Device Having Illumination Devices FIGS. 11A-11C show an exemplary method for deploying the device halves (132, 134) of tissue compression device (130) within the small intestine (5) of a patient, using first and second endoscopes (170, 172). While specific reference is made below to the duodenum (8) and the ileum (12), it will be understood that this exemplary procedure may be used for deploying the device halves (132, 134) at various other locations within the gastrointestinal tract (2), or within other organs, at which an anastomosis is to be formed.

Referring to FIG. 11A, the first device half (132) is loaded onto a retractable inner member (174) of the first endoscope (170), and the second device half (134) is loaded onto a retractable inner member (176) of the second endoscope (172). Prior to or shortly after loading the device halves (132, 134) onto the retractable inner members (174, 176), but before deploying the device halves (132, 134) within the patient, the actuator element (168) of each device (132, 134) may be manipulated to move each switch (152) to its closed position to activate the illumination devices (156). Once the illumination devices (156) have been activated, the first endoscope (170) is inserted through a first natural body orifice (e.g., mouth) at a first end of the patient's gastrointestinal tract (2), and the second endoscope (172) is inserted through a second natural body orifice (e.g., rectum) located at a second end of the gastrointestinal tract (2). The distal ends of the endoscopes (170, 172), loaded with the device halves (132, 134), are routed through the gastrointestinal tract (2), from opposing directions, toward a site at which an anastomosis is to be formed.

Referring to FIG. 11B, the exemplary site for anastomosis formation is shown selected at adjacent portions of the patient's duodenum (8) and ileum (12). As the device halves (132, 134) approach the anastomosis site, light emitted by first device half (132) will transmit through the sidewalls of the duodenum (8) and ileum (12) and will become visible to the second endoscope (172). Simultaneously, light emitted by the second device half (134) will also transmit through the sidewalls (8, 12) and become visible to the first endoscope (170). A medical professional operating the endoscopes (170, 172) may then manipulate the endoscopes (170, 172) further as needed to align the first device half (132) with the light emitted by the second device half (134), and simultaneously align the second device half (134) with the light emitted by the first device half (132), thereby initially and approximately aligning the device halves (132, 134) with one another. As the device halves (132, 134) are directed closer together toward the confronting tissue sidewalls (8, 12), their magnetic members (140) mutually attract one another through the sidewalls (8, 12) and draw the device halves (132, 134) together in a finally aligned arrangement, compressing the sidewalls (8, 12) therebetween, as shown in FIG. 11C.

Referring to FIG. 11C, the device halves (132, 134) have magnetically drawn together against the tissue sidewalls (8, 12), thereby securing the device halves (132, 134) in place relative to each other and relative to the sidewalls (8, 12). The inner members (174, 176) of the endoscopes (170, 172) may then be detached from the device halves (132, 134), and the endoscopes (170, 172) may be removed from the patient by reversing them through the gastrointestinal tract (2). The device halves (132, 134) may continue to clamp the tissue (8, 12) therebetween to induce ischemia and necrosis, and eventual formation of an anastomosis as described above in connection with FIGS. 8A-8C.

In some versions, one or both illumination devices (156) of device halves (132, 134) may be configured to transition from a first illumination mode to a visibly different second illumination mode to provide an operator with a visual indication that one or more predetermined operating conditions are present. By way of example only, each illumination device (156) may be configured to emit light of a first color during the initial positioning and alignment steps shown in FIGS. 11A and 11B. Each illumination device (156) may be further configured to emit light of a visibly different second color once the device halves (132, 134) have magnetically coupled together and have fully aligned with one another so as to exert a compression force of adequate degree on the tissue sidewalls (8, 12) for forming an anastomosis therebetween, as shown in FIG. 11C. In other versions, the illumination modes may differ by light characteristics other than color, such as light intensity or frequency of emission (e.g., continuous versus blinking), for example. The change in illumination modes may be visually observed by the operator through sight windows (166) on device halves (132, 134). Alternatively, or in addition, the bodies of device halves (132, 134) may be formed of a transparent or translucent material that permits transmission therethrough of light emitted by the illumination devices (156), which light may then be observed by the operator. In versions in which the devices halves (132, 134) include mechanical latching members, such as those disclosed in U.S. patent application Ser. No. 15/419,086, issued as U.S. Pat. No. 10,206,682 on Feb. 19, 2019, transition to the second illumination mode may serve to indicate engagement of the latching members.

To enable the illumination devices (156) to operate in multiple illumination modes as described above, each circuit assembly (148) may further include one or more switches or sensors (not shown) configured to detect a predetermined condition. Such sensors may include a hall effect sensor, a pressure sensor, or a proximity sensor, for example. In one example, each device half (132, 134) may include a switch and a projection configured to actuate the switch of the opposing device half (132, 134) when the halves (132, 134) draw together. Actuation of the switches may then initiate a transition from the first illumination mode to the second illumination mode. In some versions, each circuit assembly (148) may further include a controller (not shown) that communicates with the switches and/or sensors and also with the illumination device (156) to control the transition from the first illumination mode to the second illumination mode. Various other suitable electrical components known in the art may also be included to enable effective transition between illumination modes.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A tissue compression device for forming an anastomosis between first and second anatomical structures, the device comprising: (a) a first device portion; (b) a second device portion configured to mate with the first device portion, wherein the first and second device portions are configured to magnetically draw together to compress tissue positioned therebetween; and (c) a circuit assembly carried by the tissue compression device, wherein the circuit assembly includes an electrical element and a battery configured to energize the electrical element.

Example 2

The tissue compression device of Example 1, wherein the electrical element includes at least one of an electromagnet or an illumination device.

Example 3

The tissue compression device of any one or more of Examples 1 through 2, wherein the circuit assembly is carried by the first device portion, the device further comprising a second circuit assembly carried by the second device portion and including a second electrical element and a second battery configured to energize the second electrical element.

Example 4

The tissue compression device of Example 3, wherein at least one of the electrical elements includes an electromagnet.

Example 5

The tissue compression device of Example 4, wherein the electrical element of the circuit assembly carried by the first device portion includes at least one first electromagnet, and the second electrical element of the second circuit assembly carried by the second device portion includes at least one second electromagnet.

Example 6

The tissue compression device of Example 5, wherein the at least one first electromagnet of the first device portion includes a first pair of electromagnets, and the at least one second electromagnet of the second device portion includes a second pair of electromagnets.

Example 7

The tissue compression device of Example 6, wherein the first pair of electromagnets of the first device portion includes a first inductor arranged at a first end of the first device portion and a second inductor arranged at a second end of the first device portion, and wherein the second pair of electromagnets of the second device portion includes a first inductor arranged at a first end of the second device portion and a second inductor arranged at a second end of the second device portion.

Example 8

The tissue compression device of any one or more of Examples 3 through 7, wherein at least one of the electrical elements includes an illumination device.

Example 9

The tissue compression device of Example 8, wherein the electrical element of the circuit assembly carried by the first device portion includes a first illumination device, and the second electrical element of the second circuit assembly carried by the second device portion includes a second illumination device.

Example 10

The tissue compression device of any one or more of Examples 1 through 9, further comprising a switch movable between an open position in which the electrical element is deenergized and a closed position in which the electrical element is energized by the battery.

Example 11

The tissue compression device of Example 10, wherein the switch is biased toward the closed position.

Example 12

The tissue compression device of any one or more of Examples 10 through 11, in combination with an applier instrument configured to couple to the tissue compression device and maintain the switch in the open position.

Example 13

The tissue compression device of any one or more of Examples 1 through 12, wherein the electrical element is arranged inwardly of an outer periphery of the device.

Example 14

The tissue compression device of any one or more of Examples 1 through 13, wherein the first device portion includes a first recessed base wall and the second device portions includes a second recessed base wall, and the first and second device portions combine to define a closed interior cavity bounded by the first and second recessed base walls.

Example 15

The tissue compression device of any one or more of Examples 1 through 14, wherein the first device portion includes a first mating surface having a first contour, and the second device portion includes a second mating surface having a second contour configured to complement the first contour when the first and second device portions are mated together.

Example 16

A tissue compression device for forming an anastomosis between first and second anatomical structures, the device comprising: (a) a first device portion having a first magnetic member; (b) a second device portion having a second magnetic member, wherein the first and second magnetic members are configured to draw the first and second device portions together to compress tissue positioned therebetween; and (c) a circuit assembly carried by the tissue compression device, wherein the circuit assembly includes a battery.

Example 17

The tissue compression device of Example 16, wherein the first magnetic member includes a first electromagnet and the second magnetic member includes a second electromagnet, and the electromagnets are electrically coupled to the battery.

Example 18

The tissue compression device of any one or more of Examples 16 through 17, wherein the circuit assembly further includes an illumination device electrically coupled to the battery.

Example 19

A tissue compression device for forming an anastomosis between first and second anatomical structures, the device comprising: (a) a first device half including a first circuit assembly having a first electrical element and a first battery configured to energize the first electrical element; and (b) a second device half including a second circuit assembly having a second electrical element and a second battery configured to energize the second electrical element; wherein the first and second device halves are configured to magnetically draw together to compress tissue positioned therebetween.

Example 20

The tissue compression device of Example 19, wherein each of the first and second electrical elements includes an electromagnet or an illumination device

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the devices may be disassembled, and any number of the particular pieces or parts of the devices may be selectively replaced or removed in any combination. Upon cleaning and/or replacement of particular parts, some versions of the devices may be reassembled for subsequent use either at a reconditioning facility, or by a user immediately prior to a procedure. Those skilled in the art will appreciate that reconditioning of a devices may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue compression device for forming an anastomosis between first and second anatomical structures, the device comprising:
    (a) a first device portion;
    (b) a second device portion configured to mate with the first device portion, wherein the first and second device portions are configured to magnetically draw together to define a device body that compresses tissue to induce necrosis of the compressed tissue; and
    (c) a circuit assembly carried by the tissue compression device, wherein the circuit assembly includes:
        (i) an electrical element,
        (ii) a power source configured to energize the electrical element, and
        (iii) a switch mounted to the device body, wherein the switch is configured to electrically couple the electrical element with the power source,
    wherein the first and second device portions are configured to mate together, wherein the power source is housed within the device body.

2. The tissue compression device of claim 1, wherein the electrical element includes at least one of an electromagnet or an illumination device.

3. The tissue compression device of claim 1, wherein the circuit assembly is carried by the first device portion, the device further comprising a second circuit assembly carried by the second device portion and including a second electrical element and a second power source configured to energize the second electrical element.

4. The tissue compression device of claim 3, wherein at least one of the electrical elements includes an electromagnet.

5. The tissue compression device of claim 4, wherein the electrical element of the circuit assembly carried by the first device portion includes at least one first electromagnet, and the second electrical element of the second circuit assembly carried by the second device portion includes at least one second electromagnet.

6. The tissue compression device of claim 5, wherein the at least one first electromagnet of the first device portion includes a first pair of electromagnets, and the at least one second electromagnet of the second device portion includes a second pair of electromagnets.

7. The tissue compression device of claim 3, wherein at least one of the electrical elements includes an illumination device.

8. The tissue compression device of claim 7, wherein the electrical element of the circuit assembly carried by the first device portion includes a first illumination device, and the second electrical element of the second circuit assembly carried by the second device portion includes a second illumination device.

9. The tissue compression device of claim 1, wherein the switch is biased toward a closed position.

10. The tissue compression device of claim 1, in combination with an applier instrument configured to couple to the tissue compression device and maintain the switch in an open position.

11. The tissue compression device of claim 1, wherein the electrical element is arranged inwardly of an outer periphery of the device body.

12. The tissue compression device of claim 1, wherein the first device portion includes a first recessed base wall and the second device portion includes a second recessed base wall, and the first and second device portions combine to define a closed interior cavity bounded by the first and second recessed base walls.

13. The tissue compression device of claim 1, wherein the first device portion includes a first mating surface having a first contour, and the second device portion includes a second mating surface having a second contour configured to complement the first contour when the first and second device portions are mated together.

14. The tissue compression device of claim 1, wherein the switch includes a single-pole, single-throw switch.

15. A tissue compression device for forming an anastomosis between first and second anatomical structures, the device comprising:
(a) a first device portion having:
 (i) a first elongate body,
 (ii) a first electromagnet housed within a first end of the first elongate body, and
 (iii) a second electromagnet housed within an opposed second end of the first elongate body;
(b) a second device portion having:
 (i) a second elongate body,
 (ii) a third electromagnet housed within a first end of the second elongate body, and
 (iii) a fourth electromagnet housed within an opposed second end of the second elongate body, wherein the first and second electromagnets are configured to magnetically attract the third and fourth electromagnets and thereby draw the first and second device portions together to compress tissue positioned therebetween to induce necrosis of the compressed tissue; and
(c) a circuit assembly carried by the tissue compression device, wherein the circuit assembly includes a battery housed within one of the first body or the second body, wherein the battery is configured to energize at least one of the first and second electromagnets or the third and fourth electromagnets.

16. The tissue compression device of claim 15, wherein the first magnetic member includes a first electromagnet and the second magnetic member includes a second electromagnet, and the electromagnets are electrically coupled to the battery.

17. The tissue compression device of claim 15, wherein the circuit assembly further includes an illumination device electrically coupled to the battery.

18. The tissue compression device of claim 15, wherein the circuit assembly comprises a first circuit assembly having a first battery housed within the first elongate body and configured to energize the first and second electromagnets, wherein the tissue compression device further comprises a second circuit assembly having a second battery housed with the second elongate body and configured to energize the third and fourth electromagnets.

19. A tissue compression device for forming an anastomosis between first and second anatomical structures, the device comprising:
(a) a first device half including a continuously rounded outer periphery in a direction transverse to a length of the first device half and a first circuit assembly having:
 (i) a first electrical element, and
 (ii) a first battery configured to energize the first electrical element; and
(b) a second device half including a continuously rounded outer periphery in a direction transverse to a length of the second device half and a second circuit assembly having:
 (i) a second electrical element, and
 (ii) a second battery configured to energize the second electrical element;
wherein the first and second device halves are configured to magnetically draw together to compress tissue positioned therebetween to induce necrosis of the compressed tissue,
wherein the first device half includes a first recessed base wall and the second device half includes a second recessed base wall, wherein the first and second device halves are configured to combine to define a device body having a rounded outer periphery, a length greater than a width of the device body, and a closed interior cavity bounded by the first and second recessed base walls.

20. The tissue compression device of claim 19, wherein each of the first and second electrical elements includes an electromagnet or an illumination device.

* * * * *